United States Patent
Silverman

(12)
(10) Patent No.: US 6,340,359 B1
(45) Date of Patent: Jan. 22, 2002

(54) PROCESS FOR REVERSIBLY COMPRESSING PRECHANNELLED/ PREWEAKENED DIAPHRAGMS

(76) Inventor: David G. Silverman, 3 Meeker Hill Rd., Redding, CT (US) 06896

( * ) Notice: Subject to any disclaimer, the term of this patent is extended or adjusted under 35 U.S.C. 154(b) by 0 days.

(21) Appl. No.: 08/994,097

(22) Filed: Dec. 19, 1997

Related U.S. Application Data

(60) Provisional application No. 60/033,720, filed on Dec. 20, 1996.

(51) Int. Cl.⁷ ............................................... A61B 19/00
(52) U.S. Cl. ...................................................... 604/415
(58) Field of Search ................................ 606/144, 148, 606/195; 604/415, 272; 92/57; 220/89.2

(56) References Cited

U.S. PATENT DOCUMENTS 4,471,779 A * 9/1984 Antoshkiw et al. ......... 606/195
4,619,651 A * 10/1986 Kopfer et al. ............... 604/415
4,669,626 A * 6/1987 Mozley ...................... 220/89.2
5,088,996 A * 2/1992 Kopfer et al. ............... 604/415
5,417,699 A * 5/1995 Klein et al. ................. 606/144
5,478,328 A * 12/1995 Silverman et al. .......... 604/272

* cited by examiner

Primary Examiner—Thomas P. Noland
Assistant Examiner—Jay L. Politzer
(74) Attorney, Agent, or Firm—Ostrolenk, Faber, Gerb & Soffen, LLP

(57) ABSTRACT

A process of reversibly increasing a compression pressure on a compromised diaphragm, which comprises the steps of compromising the diaphragm to enhance its penetrability; then applying pressure to a receptacle which encircles the diaphragm, to seal the diaphragm; then releasing the pressure; and then permitting an insertion member to permeate the diaphragm in its compromised region for fluidic communication after relief of the pressure.

21 Claims, 26 Drawing Sheets

PROCESS FOR REVERSIBLY COMPRESSING PRECHANNELLED/ PREWEAKENED DIAPHRAGMS

CROSS-REFERENCE TO RELATED APPLICATIONS

This application is based on U.S. Provisional Application Ser. No. 60/033,720 filed Dec. 20, 1996, incorporated by reference.

It is related to the applicants' prior U.S. Pat. No. 5,478, 328 issued Dec. 26, 1995, incorporated by reference.

It is also related to the applicants' other applications, incorporated by reference, filed on even date herewith, namely a three-part series of disclosures titled:

I="Strong Diaphragm/Safe Needle Units and Components for Transfer of Fluids";

II="Strong Diaphragm/Safe Needle/Converting Device Combinations and Their Individual Components"; and III="Reversibly Compressed Prechannelled/Preweakened Diaphragms for Use with Blunt Cannulae and Safe Needles".

BACKGROUND OF THE INVENTION

The present series of inventions was prompted by the obvious need to decrease the exposure of healthcare workers to potentially harmful needle sticks which, as detailed in the inventors' recent disclosure (U.S. Pat. No. 5,478,328 in 1995), pose the risk of infection with diseases such as hepatitis and AIDS. All too commonly, inadvertent needle sticks occur with needles that are being used for, or have been used for, penetrating a diaphragm. The varied uses of such needle/diaphragm combinations include: (a) withdrawing from or injecting into a medication vial, collection tube, or fluid bag; (b) injecting or withdrawing medications or fluids via tubing attached to an intravenous catheter.

The common features of the present series of inventions include needle/diaphragm combinations wherein:

(a) safe yet penetrating needles, such as those illustrated, in part, in our prior patent (U.S. Pat. No. 5,478,328) and claimed herein, are designed to provide a compromise between "penetrating but dangerous" sharp needles of traditional systems and newer "safe but nonpenetrating" blunt cannulae of needleless blunt-cannula systems (described below). The inventive needles are designed to decrease the likelihood of harmful puncture of the skin of a healthcare worker (compared to that associated with a traditional needle) by one or both of the following:
  1) lessening the pointedness of the tip;
  2) providing one or more recessed orifices as opposed to an open tip;

(b) the "strong yet penetrable" diaphragms of the present disclosures are a compromise between the "strong but (relatively) impenetrable" and the "penetrable but weak" extremes described in the prior art (described below). They are designed to:
  1) provide an intact covering or plug with a section that, at the time of clinical use, can be pierced with greater penetrability than a conventional diaphragm (which requires penetration by a traditional "penetrating but dangerous" sharp-tip needle);
  2) have the integrity and long-term shelf-life approximate to that of a conventional diaphragm and thus maintain the sterility of the enclosed contents for months or years prior to the first clinical usage of the needle/diaphragm combination;
  3) have the versatility of a conventional diaphragm (i.e., be able to cover openings with a wide range of diameters as may be found on injection ports, bottle tops, etc.);
  4) provide a snug, secure fit for the needle or cannula which pierces it and thereby prevent leakage and dislodgement;
  5) provide resealing properties after needle or cannula removal that enable the diaphragm to maintain its integrity and hence the sterility of the underlying contents for a satisfactory duration.

In addition, Disclosure #II of the three-part series introduces the concept of and means of a "converting" mechanism for modifying the diaphragm immediately prior to its first penetration for clinical use. This converts a strong diaphragm which otherwise would not be so readily penetrable by a given "safe" needle or cannula to a diaphragm which can be used in combination with said needle or cannula. This conversion may be accomplished by utilizing a device to puncture and/or slit the diaphragm (herein called a "converter").

In addition, Disclosure #III of the three-part series introduces the concept of and means of providing reversible compression of a prechannelled or preweakened diaphragm. This enables one to ensure effective closure of a preslit or preweakened region before a diaphragm has been penetrated by a needle or cannula and, in many embodiments, restoration of the ancillary pressure may secure effective closure even after penetration.

As alluded to above, prior to the present invention, two extremes of needle/diaphragm combinations have been available: 1) Strong Diaphragm/Dangerous Needle; or 2) Weak Diaphragm/Safe Cannula. These are described below:

1. Strong Diaphragm/Dangerous Needle—It traditionally was felt that, in virtually all settings, needle insertion through a diaphragm necessitated the use of a sharp needle. Known hypodermic needles for use with penetrating diaphragms typically have:
   (a) a sharp point;
   (b) an open tip.

Such needles have cutting points, formed by a beveled cut typically at an angle of approximately 45° (or less) to the longitudinal axis of the needle shaft with an opening created at the junction of the beveled edge and the needle bore. Unfortunately, these features pose a threat to anyone who comes into contact with a used needle. The sharp point increases the likelihood of skin puncture; as evidenced by the large number of injuries, relatively little force is needed to penetrate the skin during an inadvertent stick with a sharp needle. The open tip can house infected fluid or tissue (herein called an inoculum); this increases the likelihood that a needle stick will result in disease transmission. The sharp-point, open-tip construction not only increases the risk of injury to a healthcare worker during usage but also increases the likelihood of accidental injury during recapping as a consequence of missing the cap or actually piercing the side of the cap.

2) Weak Diaphragm/Safe Cannula—The newly designed "needleless" blunt-cannula systems (e.g., the InterLink System, Baxter Healthcare Corp., Deerfield Ill. in collaboration with Becton-Dickinson Co., Franklin Lakes N.J.; and the Lifeshields system, Abbott Laboratories, Abbott Park Ill.) contain a diaphragm that is modified at the time of manufacture to such a degree that it is penetrable by an "absolutely" blunt-tipped cannula (with an end that typically is 90° (flat) or hemispherical, and never with >75° angle to the longitudinal axis of the cannula shaft). The manufacture of the diaphragm (herein called a "blunt-cannula diaphragm") has been taught within the prior decade as follows:

(a) cutting a slit into the central portion of the diaphragm with a knife ("preslitting") (Jepson, Dudaran, and Finley WO89/06553 & WO90/11108 in 1989/90—Baxter).

(b) reinforcing such a preslit diaphragm by covering the main plug with a thin diaphragm portion and using a metal ferrule which remains permanently in place for securing the inner and outer members of the stopper assembly together (Hook U.S. Pat. No. 5,328,041 in 1994— Abbott). In justifying the need for his more complex process (which includes two stopper members and a ferrule), the inventor stated that this was required to maintain sterility of the contents of vials covered with a preslit diaphragm: "the same prepierced construction used in prepierced reseals cannot be implemented for the stoppers on vials because of sterility and shelf-life degradation questions."

(c) molding the diaphragm in two pieces which are joined by a penetrable hinged region (Grabenkort U.S. Pat. No. 5,403,293 in 1995—Abbott). Although Grabenkort claimed that his method of "compression molding allows the tolerances at the hinged region to be better controlled than the alternate method of cutting a slit into a rubber diaphragm (as originally described in a patent assigned to Baxter), the procedure to accomplish this appears to be more complicated as it involves the production of a stiff annular collar having a first and second annular flange.

(d) using ultrasonic heating to create a weakened portion that extends at least partially through the diaphragm's midsection. The horn and anvil of the mounting device conduct heat away from the outer surfaces, thereby allowing them to remain continuous and unbroken (Helgren U.S. Pat. No. 5,403,525 in 1995—Abbott).

Review of the earlier prior art shows that the use of a more readily penetrable diaphragm was taught 30 years previously, but none of the inventions of the prior art was designed to facilitate passage of a "safe" needle as described in the present invention. Wimmer (U.S. Pat. No. 3,653,528) taught a means of creating an indentation in the outer surface to facilitate piercing without coring by a standard hypodermic needle. Sandhage (U.S. Pat. No. 2,906,423 in 1959) described a preslit diaphragm which was puncturable by a round-tip plastic "needle" which was so blunt that it was also able to be inserted into the teat of a cow to inject medication for the treatment of mastitis; however, this required lubricant to "fill up the cut slit" after needle entry "to aid in preventing the entry of contaminant organisms." Ogle (U.S. Pat. No. 5,060,812) described diaphragms which were modified to such a degree that they were penetrable by a syringe tip or nozzle (as opposed to a needle or cannula). Garrett (U.S. Pat. No. 4,197,848 in 1980) described a resilient, impermeable membrane for a urinary irrigation system, wherein said membrane had a normally closed, resiliently deformable slit. Said slit was maintained closed by compression, but was penetrable by the blunt end of a syringe. Baxter, the assignee of that invention, noted in a subsequent disclosure (WO 90/11103) that there was still a need for a preslit injection site which "will reliably reseal . . . "

Although the blunt-cannula diaphragms of the Baxter and Abbott needleless systems tend to self-seal after blunt cannula insertion, they do not guarantee adequate shelf-life and sterility in all contexts:

a) Because they require an appreciable degree of prechannelling or weakening at the time of manufacture, they have not been recommended for prolonged drug storage even prior to first clinical use and especially after they have been penetrated by a needle or cannula. Even in the prior art configuration in which the preslit extends only partway through the blunt-cannula diaphragm, "the end of the blunt cannula will be used to tear through the remainder of the sealing member." (WO 90/11103) This necessitates a very weak "tearable" portion which may restrict shelf-life, and it leads to the potential for poor resealing as a result of the tearing process. This has led to modifications such as the two stopper members and ferrule described above (Hooks U.S. Pat. No. 5,328,041) an extra valve which serves to reinforce the potentially incompetent site of needle/cannula entry and thereby reduce the risk of leakage (Brimhall U.S. Pat. No. 5,242,393). Despite these modifications, bottles and bags that either house or transfer medication and/or fluids for extended periods of time typically are not equipped for use with the Baxter or Abbott blunt-cannula systems.

b) It is recommended that such blunt-cannula diaphragms be used only with specially designed blunt cannulae since they are prone to damage by sharp needles. Said cannulae have been described as having distal ends which are completely blunt (90° degree angle to the longitudinal axis), arcuate, or hemispherical or as having a lead post which extends beyond the end of the cannula (to guide insertion) or a taper with up to a 15° angle to the longitudinal axis. Greater tapers and actual points were avoided in large part because of the preslit/preweakened diaphragm's susceptibility to damage. The inventors of needleless systems also proposed the use of conventional lubricant "to further reduce the friction and lower the insertion force required." (WO 90/11103).

c) The blunt-cannula diaphragms only can accept blunt cannulae of limited diameter and the diaphragm itself cannot be provided in the widths required to cover variously sized bottle tops, injection ports, and collection tubes without unacceptably compromising diaphragm integrity. As stated by the inventors (WO 90/11103) of the blunt-cannula system: "To provide for leak-free insertion, the length of the slit in the sealing member must be less than one-half the circumference of the cannula being inserted therethrough [—as a consequence of the greater penetrating ability of our inventive needles, the length of the slit would not so severely limit the diameter of the fluid channel when the proposed inventive needles are used] . . . In addition, the slit length must be great enough, given the elastic limit of the sealing member, to prevent tearing during insertion." [—again, this should be less of a problem when a more tapered device (e.g., inventive needle) is used].

d) In order to accommodate a blunt cannula, the preslit typically extends to the surface or an indentation is produced so as to facilitate blunt cannula insertion. Either of these surface modifications may limit the effectiveness of antiseptic swabbing. Attempts to overcome this problem have entailed the addition of a potentially costly step in the manufacturing process, including covering the preslit stopper with a second member (which is to be torn by the blunt cannula).

The absolutely blunt cannulae of the Baxter and Abbott needleless systems also pose limitations. As stated above, they can be of only limited diameter (and thus can allow only limited flow rates) as they would otherwise require an unacceptably large slit in the diaphragm to allow insertion of their blunt tip. In addition, they tend to slip out of the blunt-cannula diaphragm, a problem that could be partially mitigated by increasing cannula length, but such a change would slow flow even further. Realizing the potential problems associated with a standard blunt cannula system, the inventors (WO 90/11103) note: "In accordance with further aspects of this invention, the blunt cannula may be provided with features that facilitate insertion into the injection site, enhance fluid flow or dispersion, increase tug resistance, and reduce kickback." These include: 1) the inclusion of a plurality of elongate discharge slits to improve flow which otherwise may be compromised by the cannula's narrow diameter as well as to decrease the contact surface area so as to facilitate insertion; 2) grooves on the side of the cannula to reduce surface area; 3) a lead post to guide cannula insertion; 4) annular barbs to reduce kickback; 5) matching locking means, gripping means, and "retaining fingers" to secure engagement. Moreover, the use of blunt cannulae necessitates modification or replacement of existing setups, so that a blunt-cannula diaphragm is always available. The use of the prior art blunt cannula in the absence of a setup with a preslit or weakened diaphragm is virtually impossible unless one inserts a special "spike" adaptor. One side of the adaptor has a sharply pointed, open-tipped spike which can pierce a standard diaphragm; the other side has a preslit diaphragm. The spike must remain in place as long as the blunt cannula is used; and it must be discarded as a potentially hazardous sharp object (akin to a "penetrating but dangerous" needle) once it is no longer required. To the best of our knowledge, there has been no attempt to increase cannula penetrating properties in a manner comparable to that of the present disclosure; i.e., there has been no obvious attempt to increase penetrating capabilities by using a tapered needle (such as those claimed in the present three-part series) and thereby allowing for an inherently stronger entry point in the diaphragm.

The limitations of needleless systems are significant to the degree that the New York State Study on Needlestick Prevention Devices (in 1992) reported that two-thirds of healthcare workers felt that special training in the use of a needleless device was required and 20.3% of the workers at a major test center believed delivery was impeded with the device. Furthermore, the report noted that, because of the inability to provide blunt-cannula diaphragms for most containers (e.g. bottles, bags), ". . . needles used with the system continued to be a hazard for injury. In one institution, needles continued to be used for administering heparin or saline 'flushes' while in the other hospital, in an attempt to avoid this hazard, a complicated system using multiple components was put into place." These factors led the compilers of the NYS report to conclude that blunt-cannula systems are less cost-effective than systems using traditional sharp, open-tipped needles enclosed in a plastic shield; thus, although they do not eliminate the potential to contact a dangerous needle, the report concluded that shielded needle systems produce "greater reductions in needlestick injuries" than the needleless systems. Of note, neither the NYS Study nor an Apr. 16, 1992 FDA Safety Alert ("Needlestick and other risks from hypodermic needles on secondary i.v. administration sets") recommended or even mentioned the use of an intrinsically safer needle (as opposed to a "safe but nonpenetrating" blunt cannula or a "penetrating but dangerous" sharp needle which is extrinsically modified with a shield). This provides strong evidence that the subject matter disclosed herein, and in the applications and patents incorporated by reference, was not apparent even to experts and leaders in this field.

SUMMARY OF THE INVENTION

The present invention is #III of a three-part series of disclosures describing "Strong Diaphragm/Safe Needle" systems and the design and use of their individual components in order to bridge the gap between the Strong Diaphragm/Dangerous Needle and Weak Diaphragm/Safe Cannula extremes of the prior art. An important feature of the present inventions is that, in contrast to the prior art, they provide healthcare worker safety while maintaining diaphragm integrity; i.e., the inventive series of needles and diaphragms avoid the need for diaphragms which are compromised to the point of having suboptimal sealing and unacceptably short shelf-lives as well as avoiding the need for sharp, open-tipped hypodermic needles or spike adaptors that pose infectious risks to healthcare workers.

In Disclosure #I of this series (titled "A Strong Diaphragm/Safe Needle Unit and Components For Transfer of Fluids"), we teach how strong diaphragm/safe needle embodiments may be achieved by customizing needles and lessening the degree of diaphragm prechannelling/preweakening at the time of manufacture (as compared to needleless systems of the prior art). Disclosure #II describes ways of further improving the effectiveness and safety of needle/diaphragm combinations by piercing the diaphragm with a convertor. The present disclosure provides another way of maintaining diaphragm integrity before and after penetration. It focuses on a design process that entails the introduction of reversible augmentation of compressive pressure, which is relieved prior to insertion of a safe insertion member. The ability to use the inventive needles described in this three-part series (as opposed to relying solely on the blunt cannulae of the prior art) allows for maintenance of a smaller diaphragm opening and/or a lesser degree of diaphragm weakening. This further limits unwanted communication between contents and environs, allows the inventive diaphragm to remain suitable for repeated use with regular as well as inventive needles (thereby obviating the need for multiple sets of supplies and bulky adaptors), and allows the inventive diaphragms to be constructed in a wide range of sizes (which may be adapted to meet medical needs without requiring a spike adaptor or standard sharp needle or the need for multiple stopper layers and leak-preventing valves).

The intrinsically safer inventive needles—which are far more versatile than the blunt cannulae of needleless systems—are achieved by customizing needles with one or both of the following:

(a) a partially blunted "safe" tip which is sharp enough to puncture the inventive diaphragm but not sharp enough to penetrate the skin under normal clinical conditions, including incidental contact or contact during recapping;

(b) a closed tip and one or more recessed orifices to minimize exposure to a sizable inoculum should superficial skin penetration occur. The increased safety afforded by the closed tip allows for the safe use of needles which are significantly more pointed than the blunt cannula of needleless systems and thus usable with a wider range of diaphragms and in a wider range of lengths and diameters. In addition, the solid tip lacks the "cutting" quality of an open-tip design and thereby should allow for more effective leak-free engagement and resealing. Moreover, to date, all reported transmissions of AIDS via puncture wounds to healthcare workers have resulted from puncture with a hollow bore device such as a traditional hypodermic needle or a broken glass tube. These present a sizeable inoculum which may be avoided with the solid-tip needles described herein.

As detailed in Disclosure #I, solid-tip needles are commercially available from many manufacturers for a variety of uses, including: spinal myelography, injection of intraspinal anesthetics, soft tissue biopsy, and perineural injections (as summarized by the present inventors in U.S. Pat. No. 5,478,328 in 1995 in which we taught that the use of a recessed-orifice needle permits the use of catheters which can be rotated to selectively overly the needle orifice(s)). No other inventor or manufacturer has even proposed the use of the recessed-orifice configuration for the purpose of healthcare worker safety.

This disclosure and its companion disclosures also teach a combined testing procedure which addresses both testing of diaphragm integrity and penetrabilty as well as relative needle safety using a combined index (described below).

BRIEF DESCRIPTION OF THE DRAWINGS

In FIG. 8c, an optional depression identifies the site for cannula/needle insertion and may facilitate such insertion. FIG. 8d shows an optional depression surrounded by a circumferential ridge.

DETAILED DESCRIPTION OF EMBODIMENTS OF THE INVENTION

Figure 1:
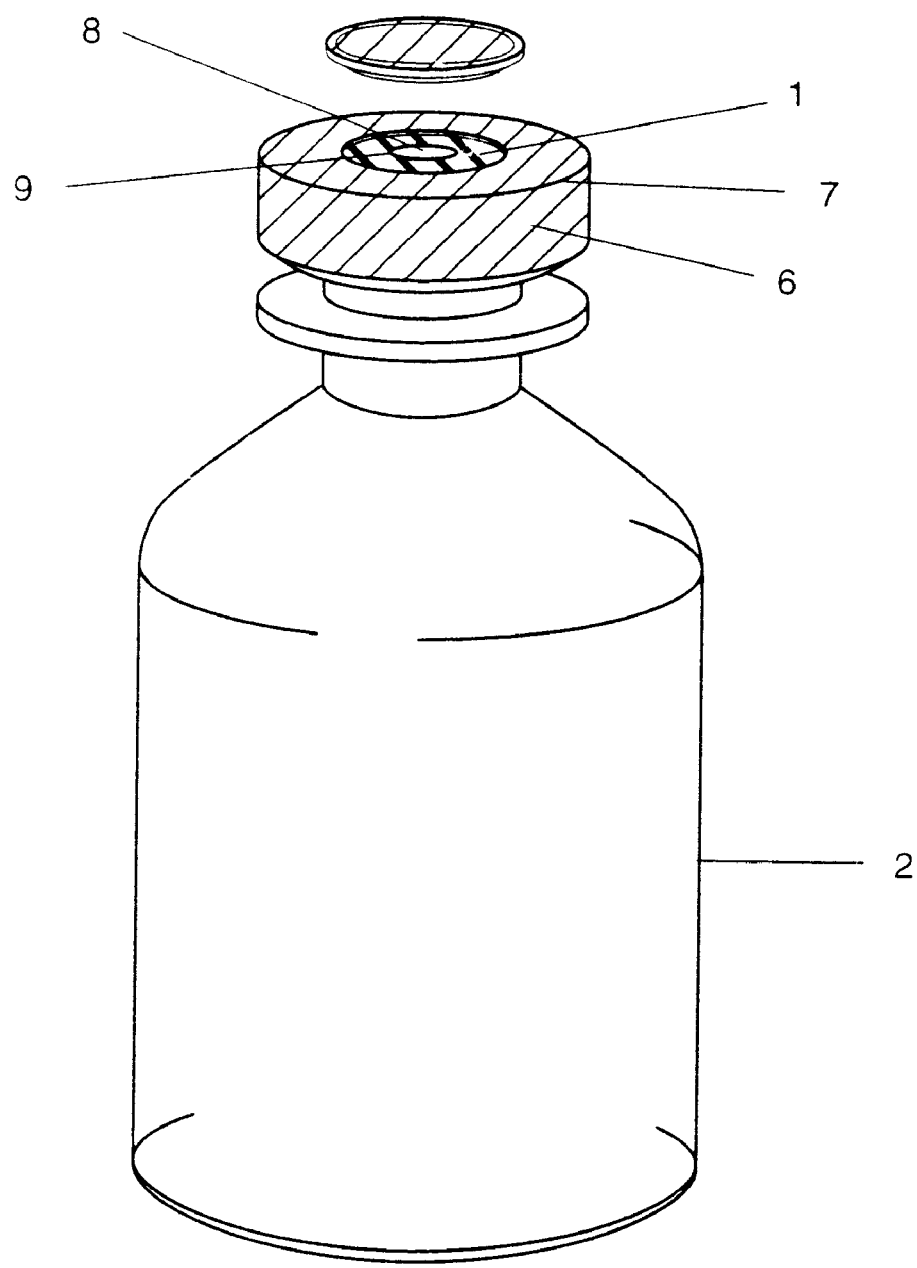
FIG. 1 shows a standard diaphragm on top of a typical medication vial.
Figure 2:
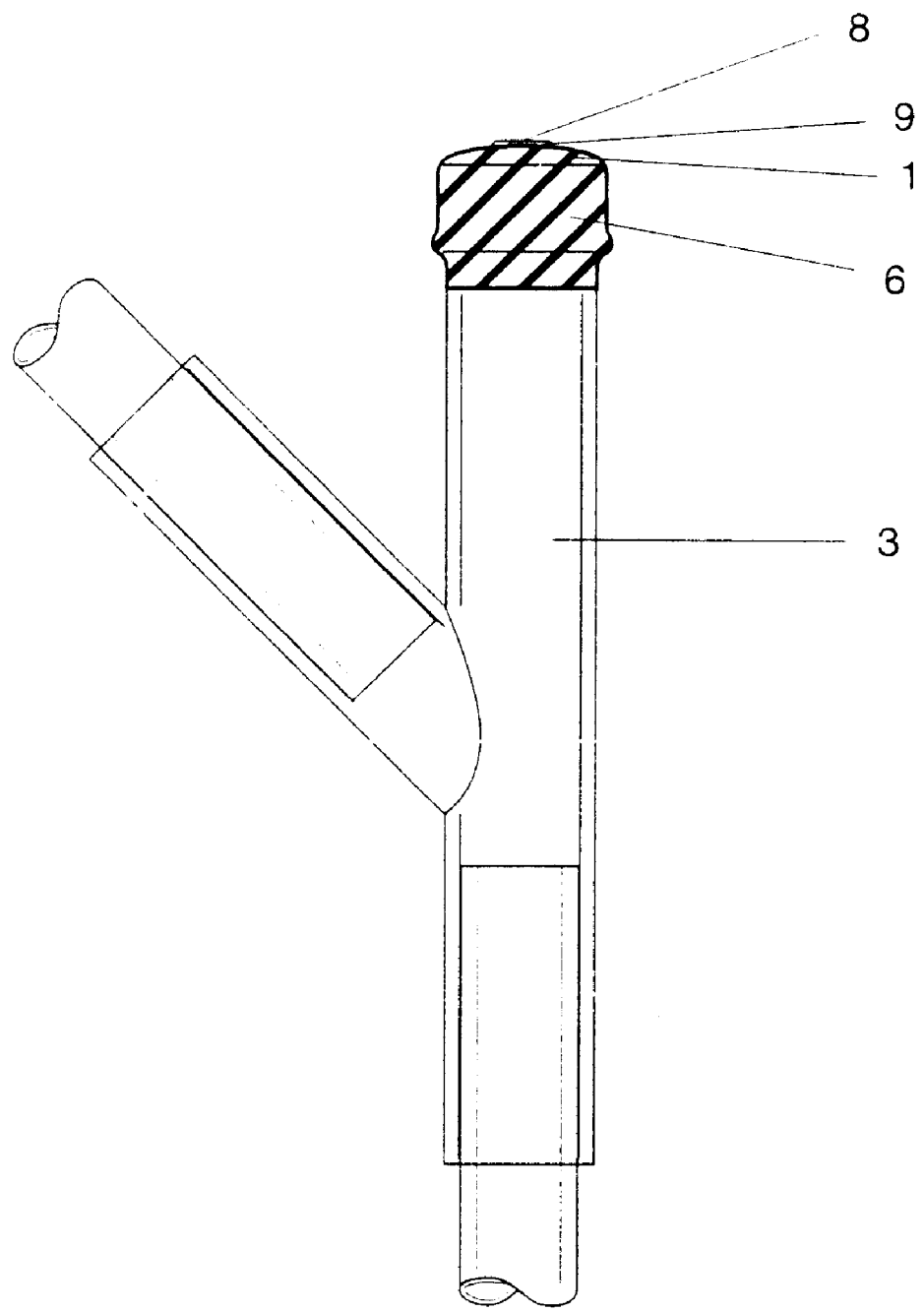
FIG. 2 shows a standard diaphragm on top of a standard injection port for intermittent infusion of medications and fluids via intravenous tubing which is connected to an indwelling intravenous catheter.
Figure 3:
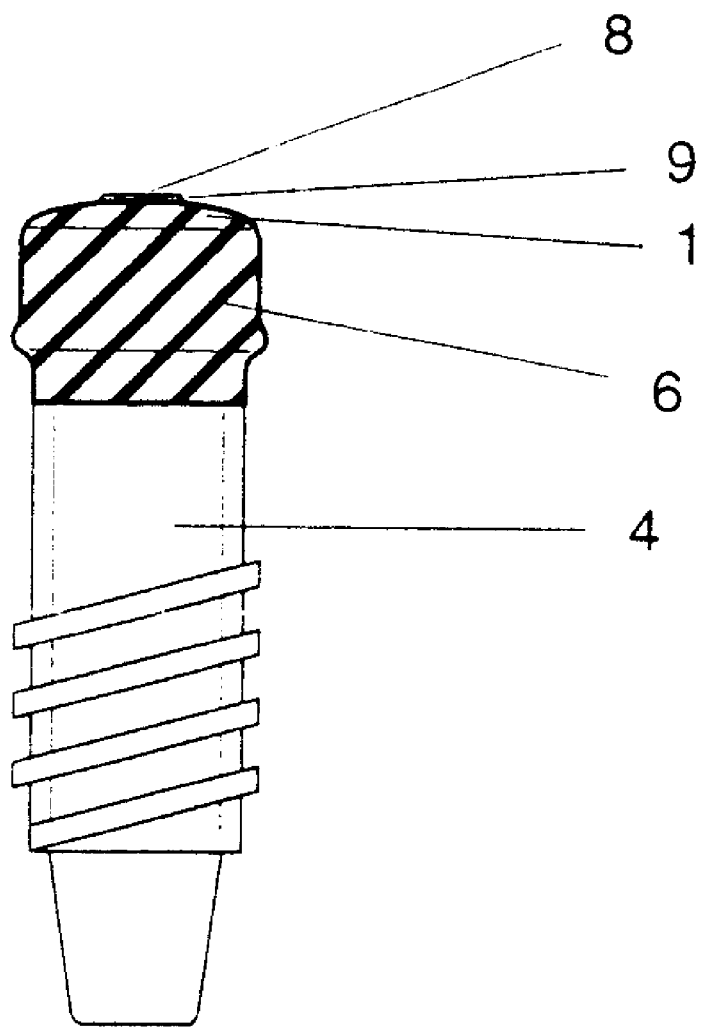
FIG. 3 shows a standard diaphragm on top of an adaptor for penetrable plugging of the nonpatient end of an indwelling catheter (e.g., a standard heparin lock for intermittent intravenous infusion of drugs).
Figure 4:
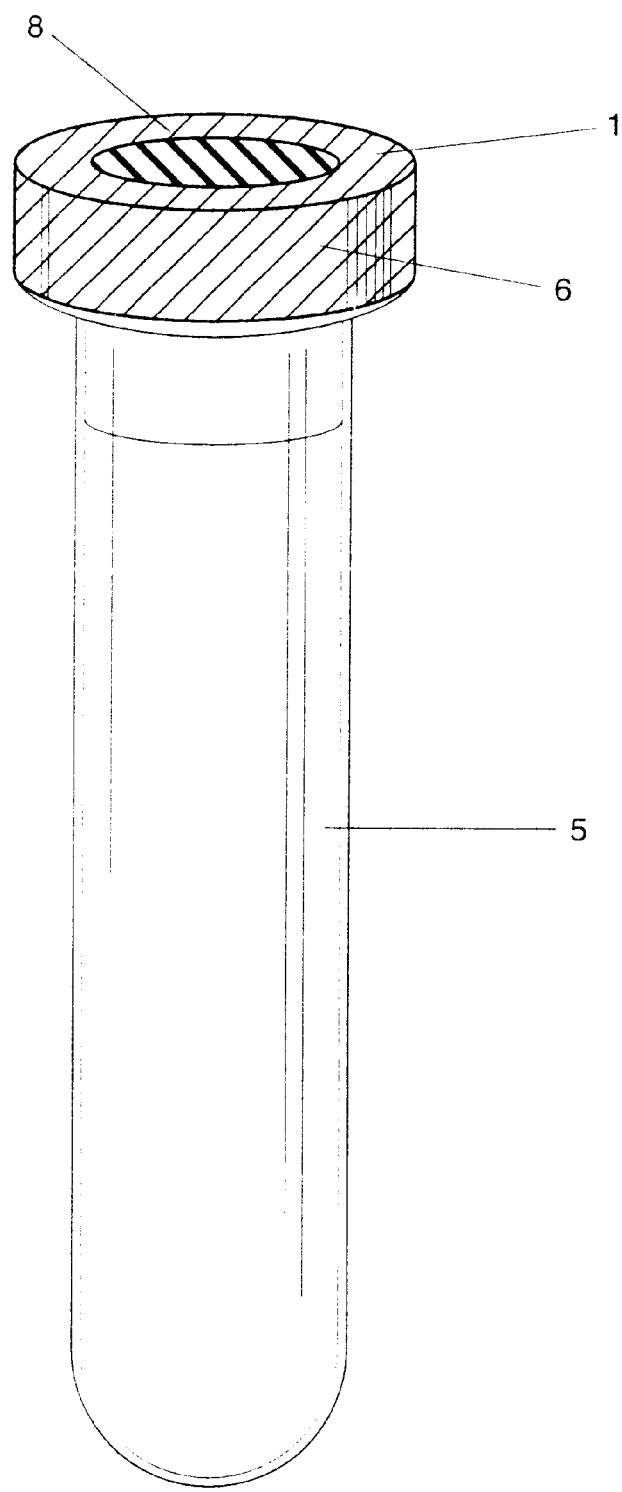
FIG. 4 shows a standard diaphragm on top of a standard vacuum tube for blood collection from a needle attached to a filled syringe or by attachment to a vacuutainer blood collection system.

The following description of the invention refers to the accompanying drawings. It will relate features of the diaphragms and safety needles of the three-part series, with special emphasis on the designs and processes for providing reversible compression. Other objects, features, and advantages of the present invention will become apparent from this description. It should be noted that we will not attempt to reteach aspects that already have been described in the prior art, such as the construction of a standard diaphragm, standard needle, or blunt cannula. It also should be noted that, although some of the individual components described in the present disclosure may in and of themselves not be unique, their use in association with other components of this three-part series has not heretofore been known. Thus, when we describe an individual component, a major distinguishing feature of the component may entail the addition/removal of the reversible compression arrangements disclosed herein. Modifications, equivalents and adaptations of specific features and the combination of features from the specific embodiments described below are intended to be within the spirit and scope of this disclosure.

The diaphragms of the present invention are designed to:
a) maintain their integrity prior to clinical use;
b) be readily penetrable to inventive needles at the time of clinical use;
c) demonstrate effective leak-free engagement and sealability during and after such use. These goals are achieved with a series of inventive diaphragms which undergo compromise (preslitting or preweakening) at the time of manufacture but nonetheless ensure leakfree shelf-life prior to needle or cannula insertion and persistent closure after insertion member removal in part as a result of reversible compression.

The diaphragm may be composed of a number of different materials. Soft, easily penetrable, resilient materials are preferred so that the diaphragm: 1) provides effective, leak-free closure; 2) has the penetrability, resilience, and memory to allow efficient insertion of the desired needles or cannulae after relief of reversible compression; 3) engages the needle effectively; and 4) has sufficient memory and resilience to reseal effectively. As noted by Sims in U.S. Pat. No. 4,846,809, diaphragms should be formed with sufficient memory so that an opening formed by a penetrating needle point will tend to close after the needle tip has been retracted beyond the membrane. Polyisoprene rubber is a preferred form of resealable rubber, although resealable latex, silicone or butyl rubber may be used. Brimhall (U.S. Pat. No. 5,242,393) has described the use of an elastically deformable thermoset elastomer, preferably Dow Corning Medical Grade Injection Moldable silicone rubber. Donnelly U.S. Pat. No. 4,513,651 taught a stopper that is a composite inner elastomer core and an annular surround plastic cap. Grippi U.S. Pat. No. 4,697,717 describes a stopper that is a composite of plastic and rubber.

In each of the embodiments, the diaphragm is housed in a retaining member. This typically is a cylindrical housing, but it may take on other forms so long as it applies axially directed forces to the sealing member. Said cylindrical housing may be at the top in order to promote sealing of the narrowed region and to provide a curved exterior peripheral surface under suitable pressure. Kleiner U.S. Pat. No. 2,607,347 (in 1952) taught that "By having the plug portion of slightly larger diameter than the bore which receives it, that portion is placed under compression as the stopper is positioned."

Thus, the prior art teaches that the sealing properties of a stopper (or diaphragm)—with or without a preslit or preweakened area—are enhanced by axial compression. However, no one has proposed or disclosed means of applying reversible compression. The application of compressive pressure can improve the shelf-life of a desirably penetrable diaphragm so that it is comparable to that of a less penetrable diaphragm. For example:
  a) a partially prechannelled diaphragm (as described in the present series of disclosures) with a partial preslit or hole that is penetrable by an inventive needle remains securely biased in the closed position such that, without prior relief of the reversible compression, it would be penetrable only by a sharp needle;
  b) a partially preweakened diaphragm (as described in the present series of disclosures) that is penetrable by an inventive needle remains securely intact such that, without prior relief of the reversible compression, it would be penetrable only by a sharp needle;
  c) a preslit diaphragm (as described in the prior art) that is penetrable by an insertion member as blunt as a blunt cannula remains biased in the closed position such that, without prior relief of the reversible compression, it would be penetrable only by a sharper insertion member (such as a dangerous sharp needle or an inventive safe needle);
  d) a preweakened diaphragm (as described in the prior art) that is penetrable by an insertion member as blunt as a blunt cannula remains securely intact such that, without prior relief of the reversible compression, it would be penetrable only by a sharper insertion member (such as a dangerous sharp needle or an inventive safe needle).

Figure 5:
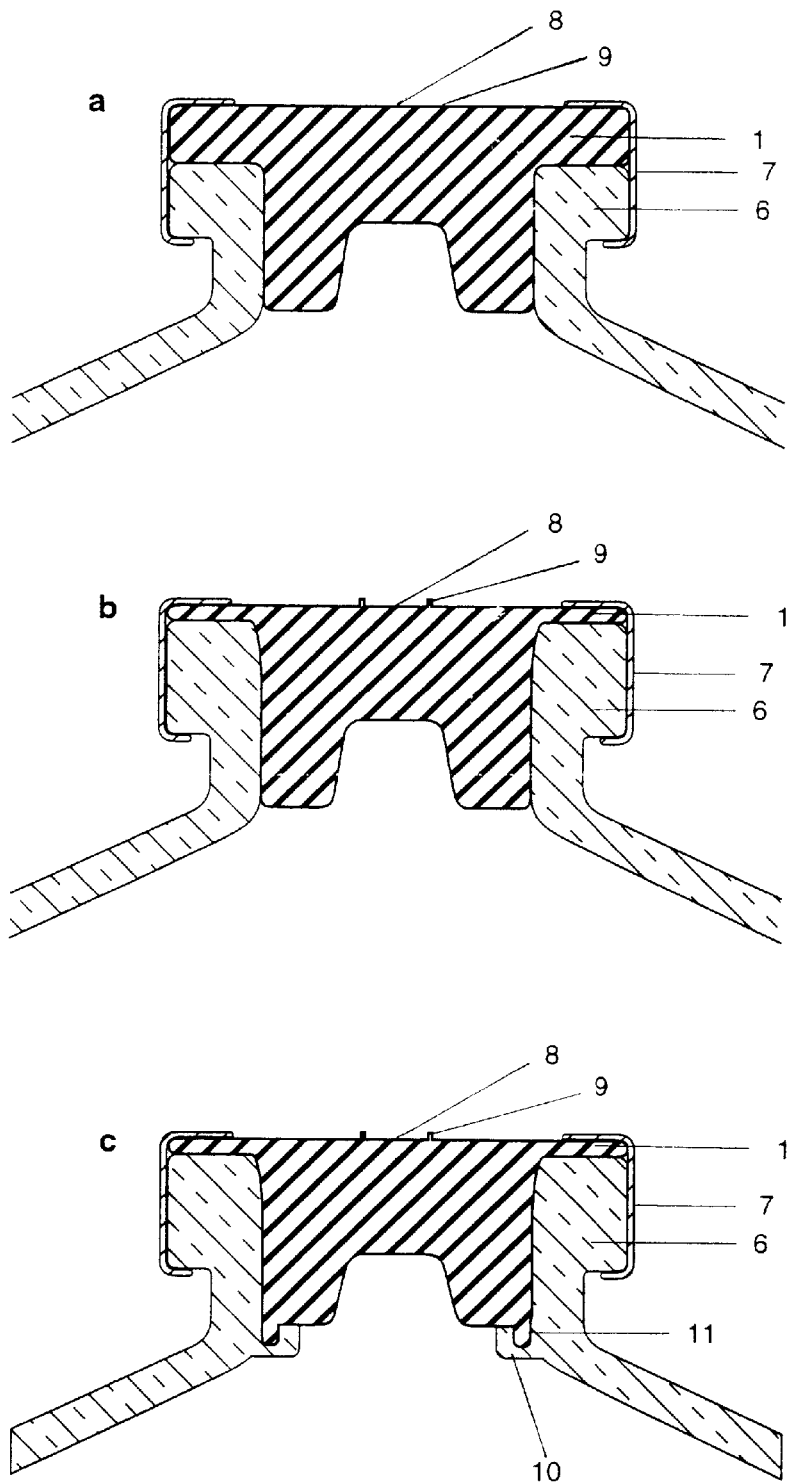
FIGS. 5a–5c are cross-sectional views of an intact (i.e., non-slit, non-weakened) compressible diaphragm which is maintained under compressive pressure in one of many potential housings which could be used in FIGS. 1–4 above.

FIGS. 1–5 show standard diaphragms 1 as taught by prior art on top of a typical medication bottle 2, an i.v. tubing injection port 3, a heparin lock for drug infusion 4, and a vacuum tube for blood collection 5. The receptacle in which the diaphragm is retained 6 provides for compressive engagement and retention. As illustrated in FIG. 5, the diaphragm may extend to varying degrees (if at all) above the receptacle 6. Retention of the diaphragm may be augmented by a rim 7 around the circumferential surface of the diaphragm. Diaphragms typically have a "soft spot" 8 which is surrounded by a raised border 9. This is the preferred site for penetration with a standard hypodermic needle. The configuration of the portion of the housing below the receptacle will depend on the nature of the underlying structure (e.g., bottle vs. i.v. tubing injection port). This portion of the housing can also be constructed so as to accommodate the displaced diaphragm when it is deformed by penetration by a needle or cannula. FIG. 5c shows a lip 10 in the housing which creates a channel 11 for this accommodation. (For purposes of simplicity, such a feature is not included in most of our illustrations of the prior art or of the present invention.)

Figure 6:
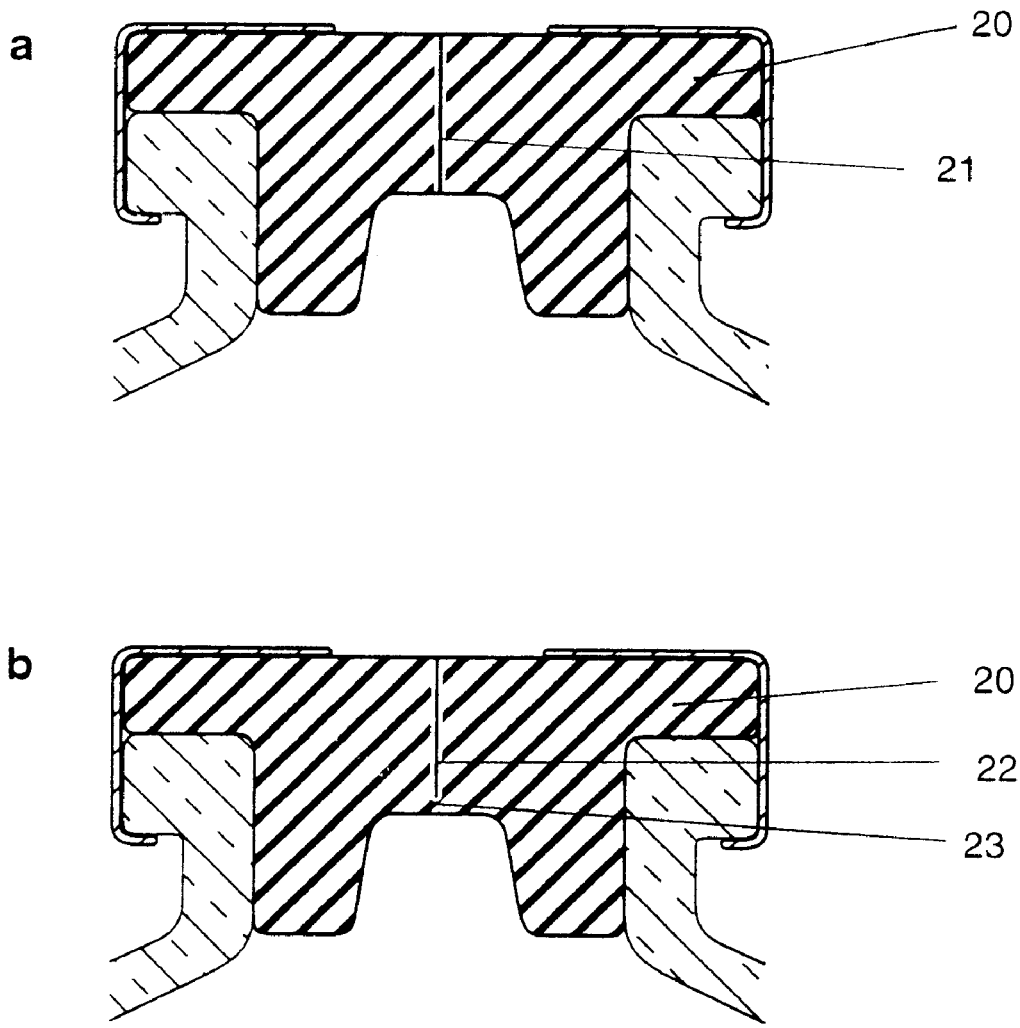
FIGS. 6a and 6b are cross-sectional views of different forms of preslit diaphragms that have been taught by the prior art, wherein the slit (which is imparted at the time of manufacture) extends all the way through or most of the way through the diaphragm.
Figure 7:
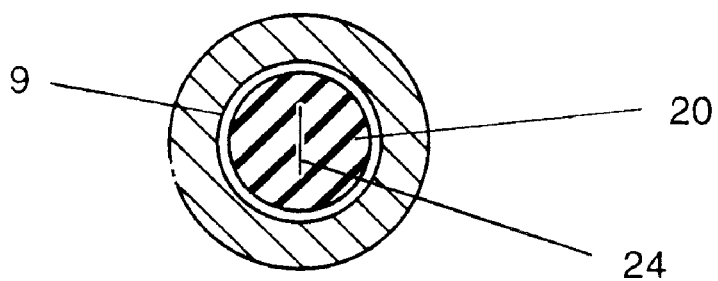
FIG. 7 is a top view of a preslit diaphragm which illustrates a slit as it appears in embodiments of the prior art.

The prior art has shown that, for needleless systems, a diaphragm may be altered at the time of manufacture to allow penetration by a blunt cannula. FIGS. 6 and 7 show prior art diaphragms 20 which have been manufactured for penetration by a blunt cannula such that they contain a slit which extends through the entire thickness of the diaphragm 21 or a slit which extends substantially therethrough 22, so as to leave a small tearable region 23. FIG. 7 shows a top view of a typical slit 24 as taught by the prior art. The prior art taught the creation of a slit that was long enough, wide enough, and deep enough to allow insertion of a blunt cannula and to minimize the need for excessive force and increased risk of tearing. However, the size of the slits was limited by their ability to ensure effective leakfree engagement and subsequent resealing. Jepson et al. (WO 90/11103) taught that the length of the slit(s) should be <½ the circumference of the cannula being inserted therethrough. Such a requirement also limited the size of the cannula; i.e., a wide cannula would require a large slit and thus the integrity of the diaphragm would be compromised even before cannula insertion.

Figure 8:
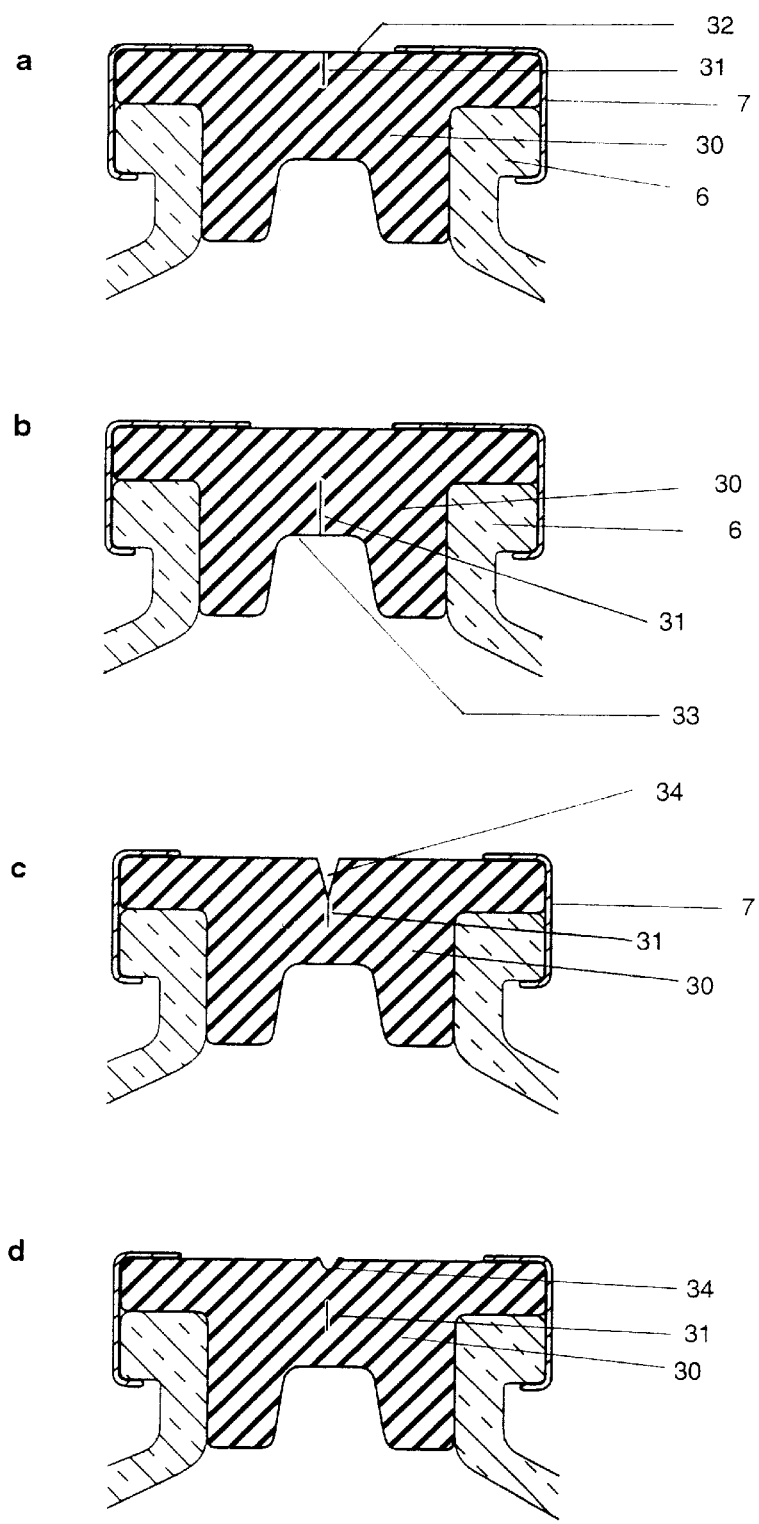
FIGS. 8a–8d are cross-sectional views of embodiments of the present invention wherein the diaphragm is preslit to a lesser degree than was required for subsequent blunt cannula penetration as taught by the prior art.
Figure 9:
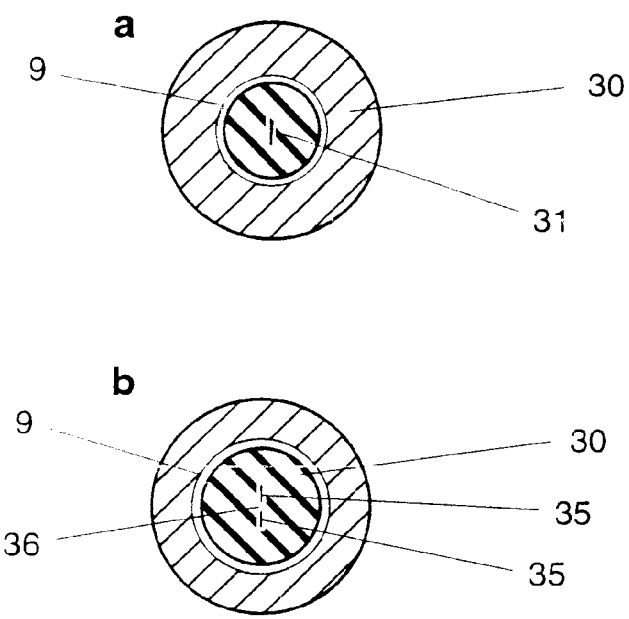
FIGS. 9a and 9b are top views as they appear in embodiments of the present series of inventions in which the preslits are incomplete and/or smaller (e.g., shorter, thinner, and/or less deep) than those required for the blunt cannula insertion of the prior art. Thus the diaphragm is compromised only slightly (in contrast to the more pronounced preslitting of prior art blunt-cannula diaphragms). Likewise, in each of the configurations, the slit may lie totally beneath the diaphragm surface.
Figure 10:
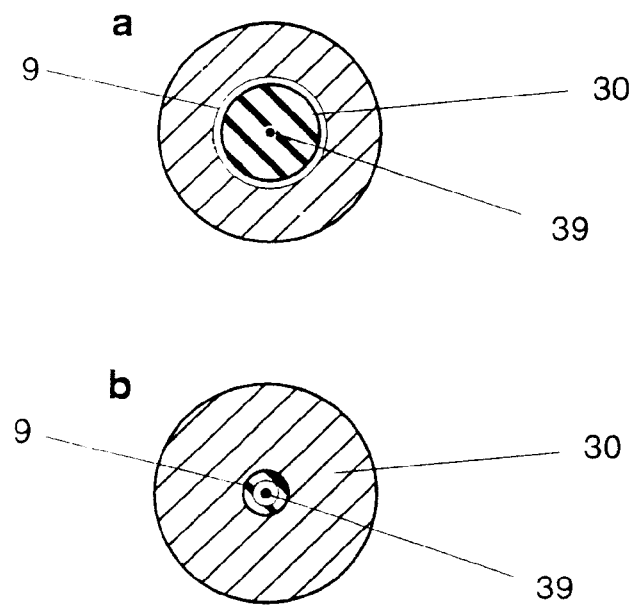
FIGS. 10a–10b are top views as they appear in embodiments of the present invention in which the diaphragm has been constructed such that the partial prechannelling entails creation of a partial hole rather than a preslit at the time of manufacture. As for the slits in FIG. 9, said hole may lie totally beneath the surface (as suggested by the shading in FIG. 10b.

FIGS. 8–10 show embodiments of the present invention wherein the inventive diaphragm 30 has a smaller prechannelled region than was required for the blunt cannula penetration taught by the prior art. The reduced channel size may be a result of a lesser degree of prechannelling at the time of manufacture (as taught by Disclosure #I of this series) or it may be as a consequence of augmented compression. FIG. 8a is a cross-sectional view of an inventive diaphragm 30 which shows a partial preslit 31 extending to the top surface 32 slit 31 which is biased in the closed position by forces as may be generated by the standard receptacle 6 or may be augmented by reversible compression as described herein. FIGS. 8b–8d show how a partial preslit 31 may arise from the bottom 33 of the diaphragm 30 and thus leave an intact, easily cleanable top surface) or from an indented region 34 at the top of the diaphragm 30. According to the present series of inventions, said partial preslits 31 could be either: used with sharper embodiments of the inventive series of needles (as detailed in Disclosure #I); deepened/widened by use of a convertor (Disclosure #II); or widened by release of compressive forces. The channels and housing can otherwise be consistent with the prior art. Consistent with the prior art, the height of the septum can be, for example, on the order of 0.125 inches (0.318 cm).

FIGS. 9a and 9b are top views which illustrate embodiments of the present invention in which the channel(s) is (are) shorter than that of the prior art and can be lengthened and/or widened by insertion of a needle. In each of the illustrated embodiments, the site of penetration is surrounded by a raised rim or flat visual identifier 9 such as a colored circle. FIG. 9a shows an embodiment of the inventive diaphragm 30 with a small slit 31. FIG. 9b shows a diaphragm 30 in which a divided slit 35 has a gap 36. For purposes of clarity, each of the embodiments shows the slit(s) extending to the top surface 32; however, the slit(s) may remain below the surface (as shown in FIGS. 8b and 8d) and thus leave the upper surface totally intact.

FIGS. 10a and 10b illustrate a hole 39, as opposed to a slit, which may be sufficient when an inventive needle is inserted through a diaphragm especially after relief of enhanced compressive pressure. Said hole may extend from the surface through the entire thickness of the diaphragm or it may extend only partway through and even lie below the surface. In the illustrated embodiment, the rim 9 encircles the recommended site of penetration. The diameter of said rim can be reduced (as in FIG. 10b) to improve the accuracy of needle insertion. A marking or depression similarly may be used to identify the optimal site of insertion.

Figure 11:
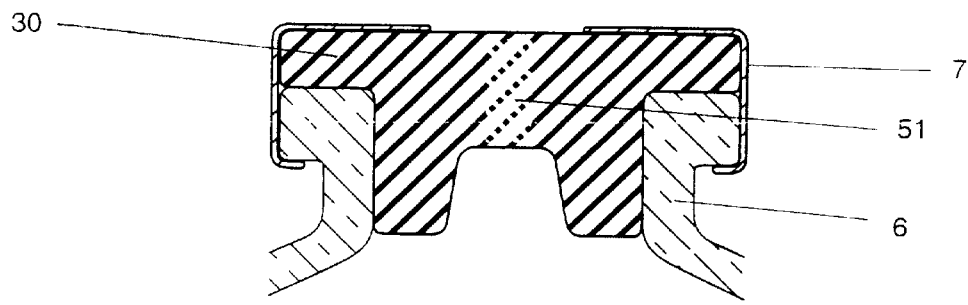
FIG. 11 is a cross-section of a diaphragm which has undergone ultrasonic weakening as described in the prior art.
Figure 12:
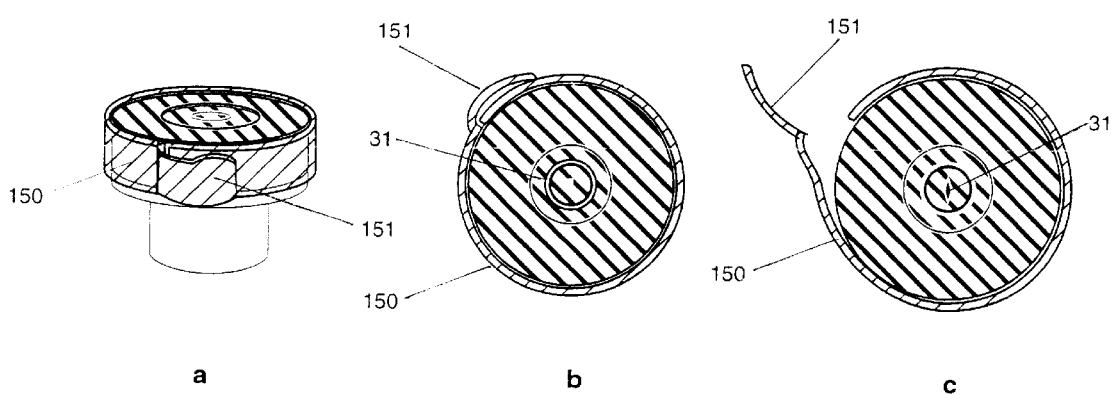
FIGS. 12a–12c illustrate a device for applying reversible compression with a removable band so as to minimize the effect of prechannelling (or preweakening) on diaphragm integrity.
Figure 13:
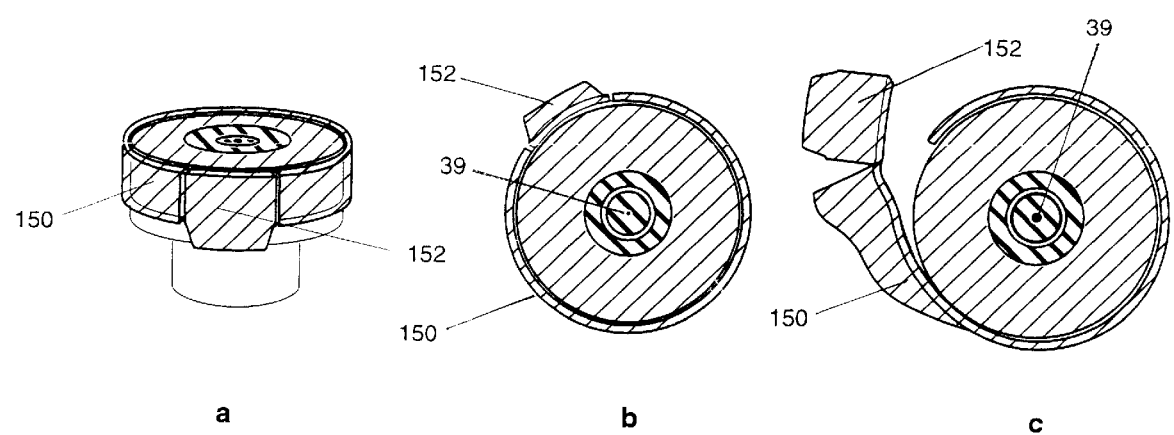
FIGS. 13a–13c illustrate an alternative compressive band configuration around a diaphragm which is prechannelled with a hole rather than a slit.

As noted in the prior art and illustrated in FIG. 11, prior art diaphragms designed for use with blunt cannulae may have a weakened area 51. One way in which this may be accomplished is by ultrasonic heating. As per a preslit region, the size and penetrability of a weakened region may be reduced by increased axial compression.

FIGS. 12–19 illustrate arrangements for applying reversible increases in axial compression so as to bias the compromised injection sites in the closed/impenetrable state. This may be achieved simply by tightly enclosing the compromised portion of the diaphragm in shrink wrap. As shown in the exemplary embodiments described below, this also may be achieved with a removable ring/collar which applies external compression or it may be achieved by occupying space within the receptacle which houses the diaphragm. Each of these devices is designed to compress the diaphragm to a greater degree than does its permanent housing. For example, if in its uncompressed state a region of a diaphragm has a diameter of 0.25 inches, this might be "permanently" compressed by its housing to between 0.20 and 0.23 inches. Our reversible compression devices may further decrease the diameter of this region to between 0.17 and 0.20 inches and thus further increase the compressive forces which bias a preslit diaphragm to the closed position. Comparable relative degrees of change in the size of the diaphragm will be achieved by the use of these devices with differently-sized diaphragms and housings which may be used to cover different receptacles.

FIGS. 12a–12c show a compressive ring 150 with a horizontal tab 151 which opens and closes a latch. Upon raising the tab 151, the ring 150 expands thereby relieving the enhanced compressive pressure and allowing the preslit 31 to expand. Said ring may be attached by a serrated junction to the overlying dust cap or to the underlying housing or it may exist independently (as shown).

FIGS. 13a–13c show a compressive ring 150 with a vertical tab 152 associated with a latch. Upon raising the tab 152, the ring 150 expands thereby relieving the enhanced compressive pressure and, in this embodiment, allowing the "prehole" 39 to enlarge.

Figure 14:
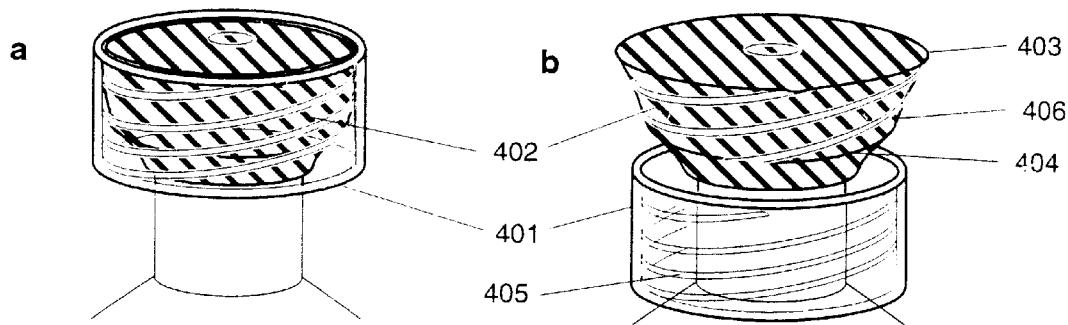
FIGS. 14a and 14b illustrate a fully displaceable collar which may be screwed onto a diaphragm to provide reversible compression.
Figure 15:
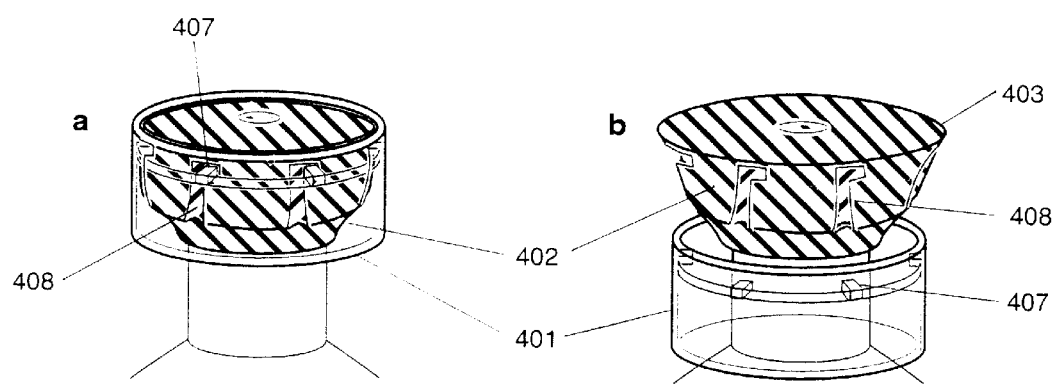
FIGS. 15a and 15b illustrate an alternate design of a fully displaceable collar which engages the outside of the diaphragm via tabs in grooves.
Figure 16:
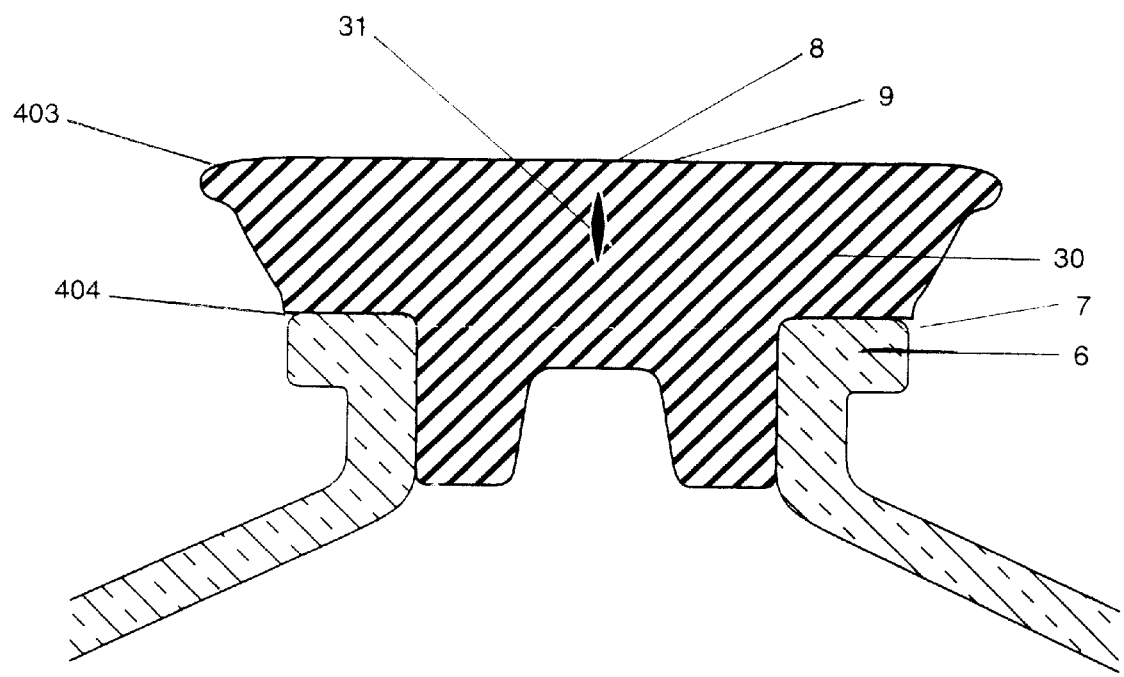
FIG. 16 is a cross-section which illustrates the potential for a region of a diaphragm to expand if it is not compressed.

FIGS. 14 and 15 illustrate a displaceable collar 401 which compresses the underlying stopper 402 which is configured so as to undergo greater reversible compression at the top 403 than at the bottom 404. In the engaged position, the engagement causes a prechannelled region to be biased to the tightly closed positions (FIGS. 14a and 15a). FIG. 14b shows that said collar 401 can be removed by disengaging the matched grooves 405 of the collar from matched grooves 406 on the stopper. This allows the stopper 402 to assume an uncompressed state which facilitates penetration by a needle or cannula. Engagement (and removal) may also be accomplished with matching tabs and grooves. FIG. 15b shows a collar 401 that may be removed by twisting and downward displacement such that the tabs 407 on the inner surface of the collar 401 are disengaged from matching grooves 408 on the outside of the stopper 402 (or vice versa). These are but two of myriad devices for reversible engagement which would be within the scope of the present invention. For example, the grooves may take on one of several configurations (many of which are illustrated for engagement of a cap plus convertor in Disclosure #II of this three-part series). Compression of the stopper 402 during engagement may be achieved as a result of outward tapering of the stopper 402 in the unengaged position (i.e., uncompressed state) such that the top surface 403 is wider than the bottom 404. This is illustrated in the cross-section of a stopper in the form of a preslit diaphragm 30 (FIG. 16), wherein the preslit region 31 is shown to be wider in the uncompressed state.

Figure 17:
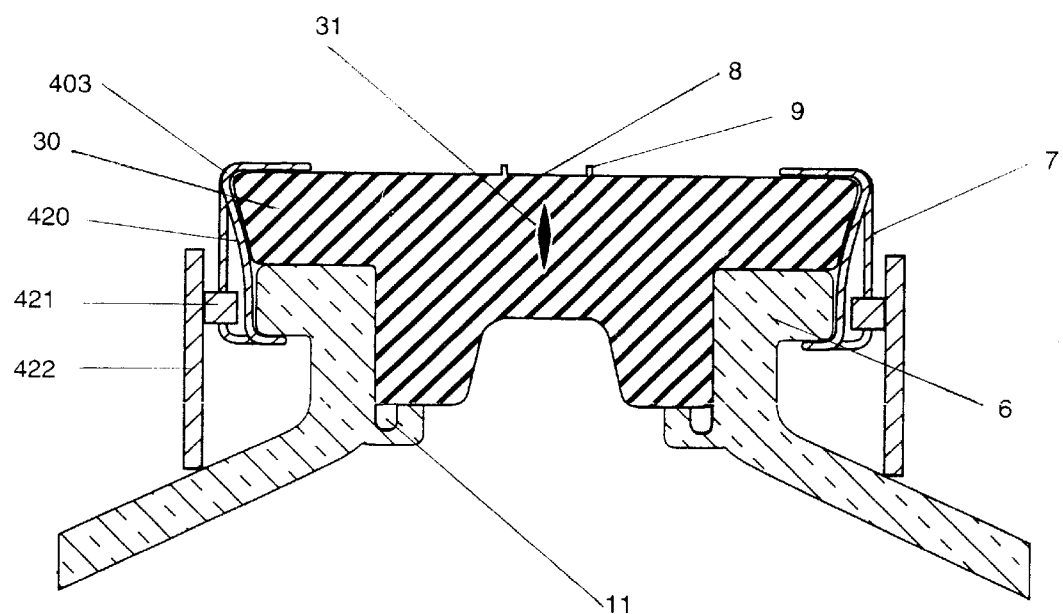
FIGS. 17 shows a partially displaceable collar which compresses the upper portion of a diaphragm when it is advanced over the rim around the diaphragm through a groove which becomes more shallow over this upper region.
Figure 18:
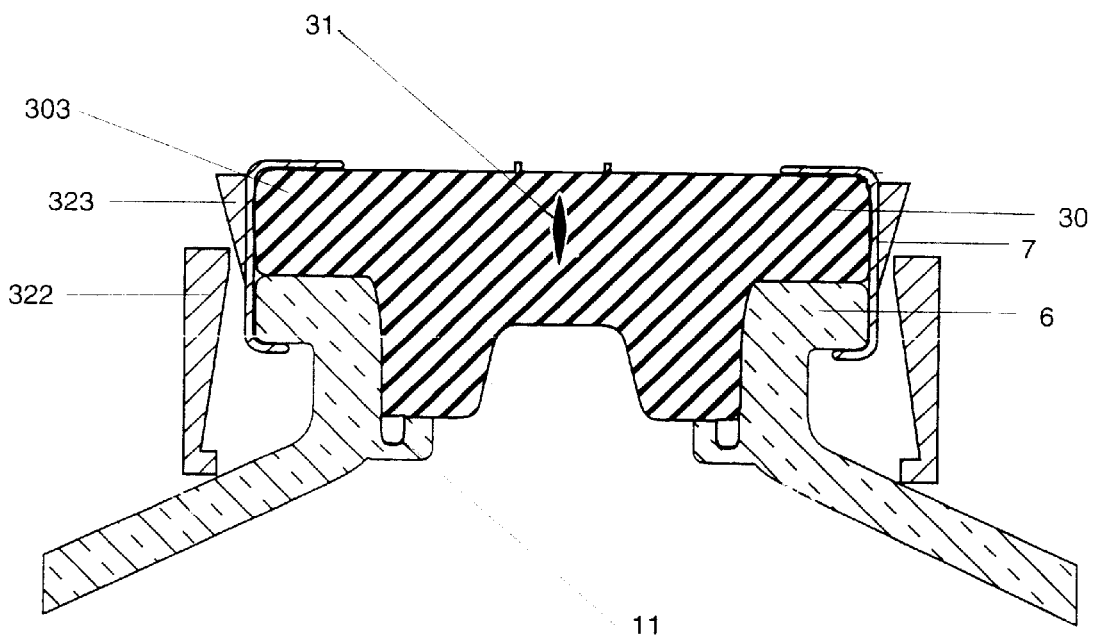
FIGS. 18 shows a partially displaceable collar which compresses the upper portion of a diaphragm when it is advanced over a ridge which becomes more prominent over this region.

Reversible compression of the preslit region (wherein the slit 31 is shown to be relatively wide in the uncompressed state) also can be achieved by configuring grooves so that they are less deep over the region where increased compressive pressure is desired. FIG. 17 shows a modified cross-section of an alternate embodiment wherein the rim 7 enclosing the diaphragm 30 (or the outer surface of the diaphragm itself) has a series of grooves 420 which are matched to tabs 421 on a displaceable collar 422 which does not completely disengage from the diaphragm 30 or its rim 7. Said grooves 420 are oriented such that they require compression of the uppermost portion 403 of the diaphragm 30 in order to allow for collar engagement at this level. Such compression can be accomplished with a number of rim/collar combinations which are disclosed in this disclosure. One alternative is shown in FIG. 18. This cross-section shows one of several portions of a rim 7 with a raised area 323 that increases in height as it approaches the top portion 303 of the diaphragm 30. Engagement of the displaceable collar 322 will result in compression of the uppermost portion 303 of the diaphragm 30 which lies above the receptacle 6. Any effective device would be suitable for this purpose, including a groove in the collar (as shown in FIG. 17) to engage the ridge on the diaphragm or a mechanism that enables pinching of the lower portion of the collar 322 or 422 to extend the upper ends so that upward movement of the collar would result in it encompassing and thus compressing the diaphragm 30 at the ridged area 323 (as shown in FIG. 18).

Figure 19:
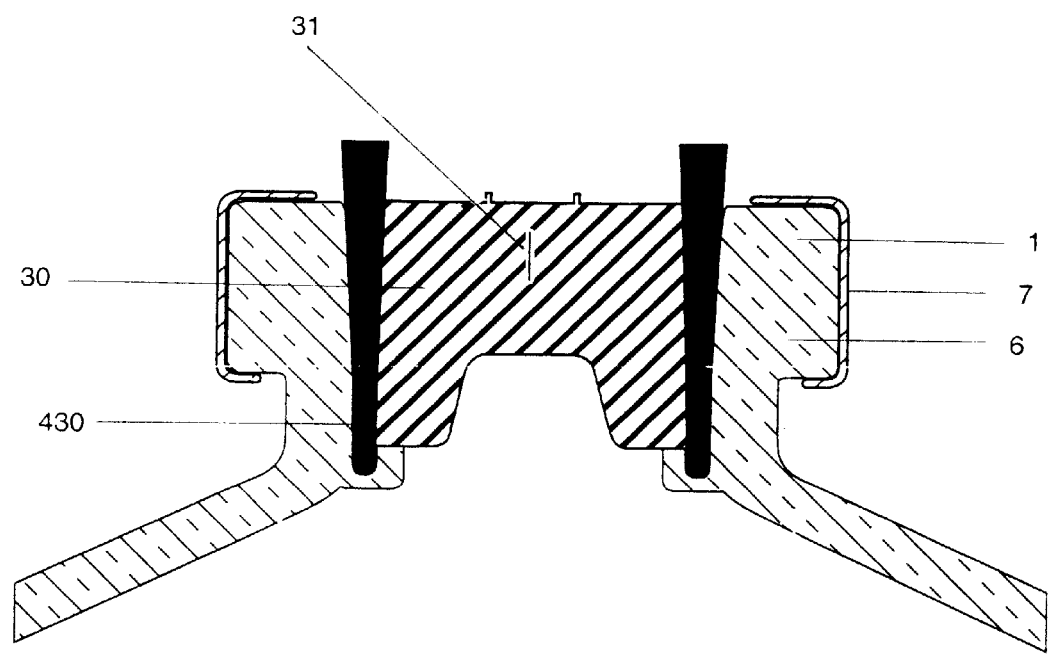
FIG. 19 shows removable pegs which may be inserted between the outer surface of a diaphragm and its receptacle so as to increase compressive pressure.

FIG. 19 shows removable pegs 430 which compress the diaphragm 30 such that the preslit 31 (or preweakened region) is biased in the closed position. Removal of the pegs 430, as may be accomplished in a separate step or simply as a part of dust cap removal, would allow expansion of the diaphragm and relief of compressive pressure.

Each of the needles of the present invention is designed to meet the following criteria: a) puncture but not tear the matched diaphragm(s); b) have a lesser likelihood of transmitting inoculum by inadvertent skin puncture as a consequence of having less likelihood of puncturing the skin than a standard hypodermic needle and/or less likelihood of exposing the victim of such a puncture to the inoculum within the hollow bore of the needle; c) allow for the use of a diaphragm with greater sealing and/or resealing properties than the preslit or preweakened diaphragm of currently described needleless systems.

As for standard hypodermic needles, the long axis of each of the inventive needles contains a hollow tubular channel (or through-bore) extending from the proximal hub end (which is structured for standard fluidic communication with other devices such as a syringe or infusion tubing) to one or more orifices located at the distal end. The orifice may be located at the end of taper. This so-called open-bevel design of the inventive series is tapered such that it is less sharp than a standard "dangerous and penetrating" needle.

Figure 20:
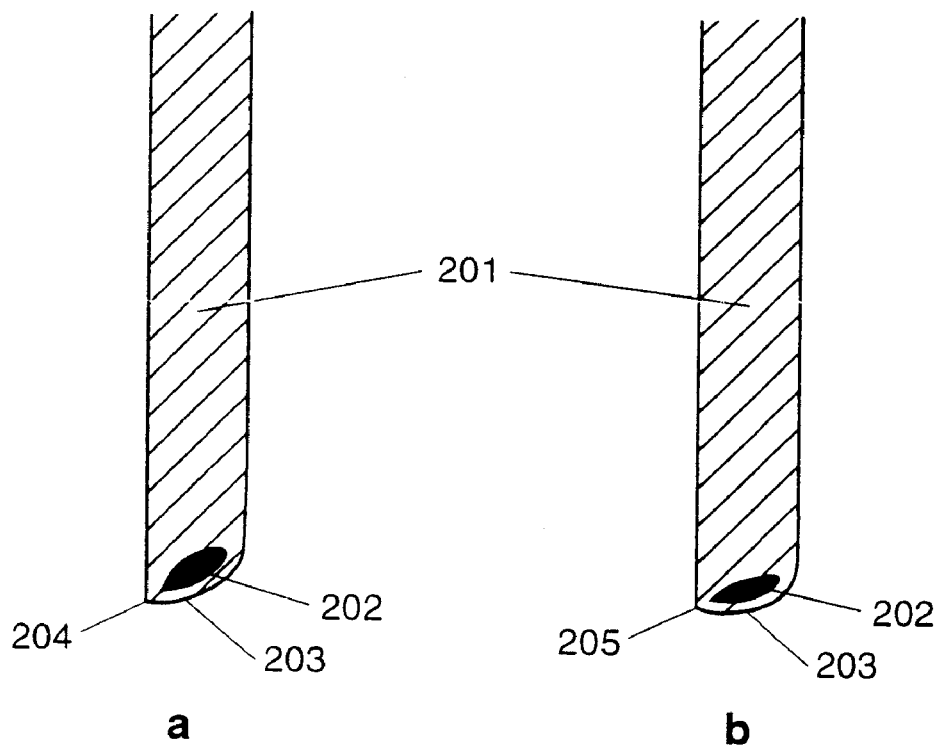
FIGS. 20a and 20b are examples of the approximate range of tapers and tips that are characteristic of the open-tipped embodiments of the inventive series of inventive needles: a) open tapered tip of approximately 30–35°; b) open tapered tip of approximately 15–20°.

FIGS. 20a and 20b show open-beveled tapered needles with a shaft 201, a tubular channel which ends in an opening 202 at the tip 203. The tip 203 may be any of several different angles to the plane which is perpendicular to the longitudinal axis of the needle, including the approximately 3020 –35° angle 204 (FIG. 20a) and the approximately 1520 –20° angle 205 (FIG. 20b).

In most of the embodiments, the orifice(s) is near, but not at, the actual tip. We believe that healthcare worker safety may be achieved more efficiently with the closed-tip design. The recessed orifices may be located at various distances from the needle tip. The hub may be marked to delineate orifice orientation. The channel may be midline or offset. The shaft may be thick-walled or thin-walled. The taper may be symmetrical or biased.

Figure 21:
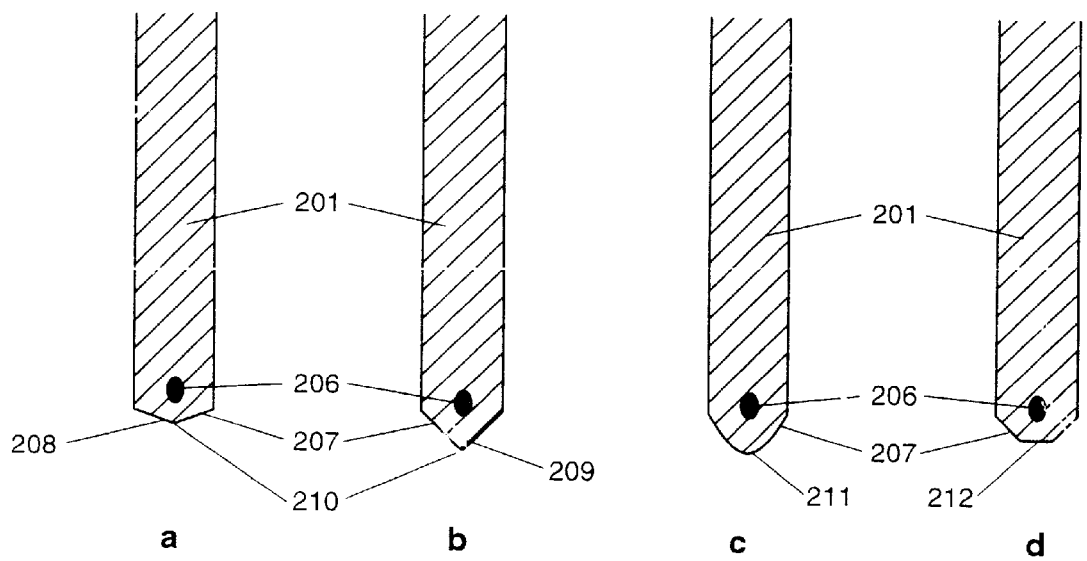
FIGS. 21a–21d are examples of the approximate range of tapers and tips that are characteristic of the closed-tipped embodiments of the inventive series: a) closed tapered tip of approximately 45°; b) closed tapered tip of approximately 20°; c) closed tapered tip with a rounded distal end; d) closed tapered tip with a flat distal end.

As illustrated in FIGS. 21a–21d, embodiments of the closed tip designs with recessed orifices 206 can have tips with tapers 207 ranging from approximately 15° (208 in FIG. 21a) to approximately 45° (209 in FIG. 21b). They may end in a pointed 210, rounded 211, or flat 212 distal end.

Figure 22:
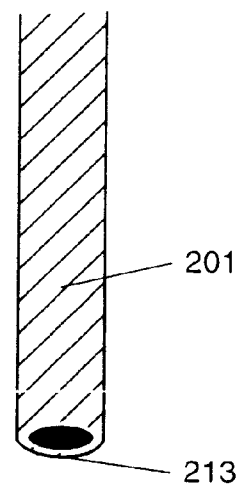
FIG. 22 shows an "absolutely" blunt cannula, consistent with that shown for needleless systems in the prior art.

Each of the tapered inventive needles can penetrate more readily than an absolutely blunt cannula (FIG. 22), whose end 213 is essentially without a taper.

Figure 23:
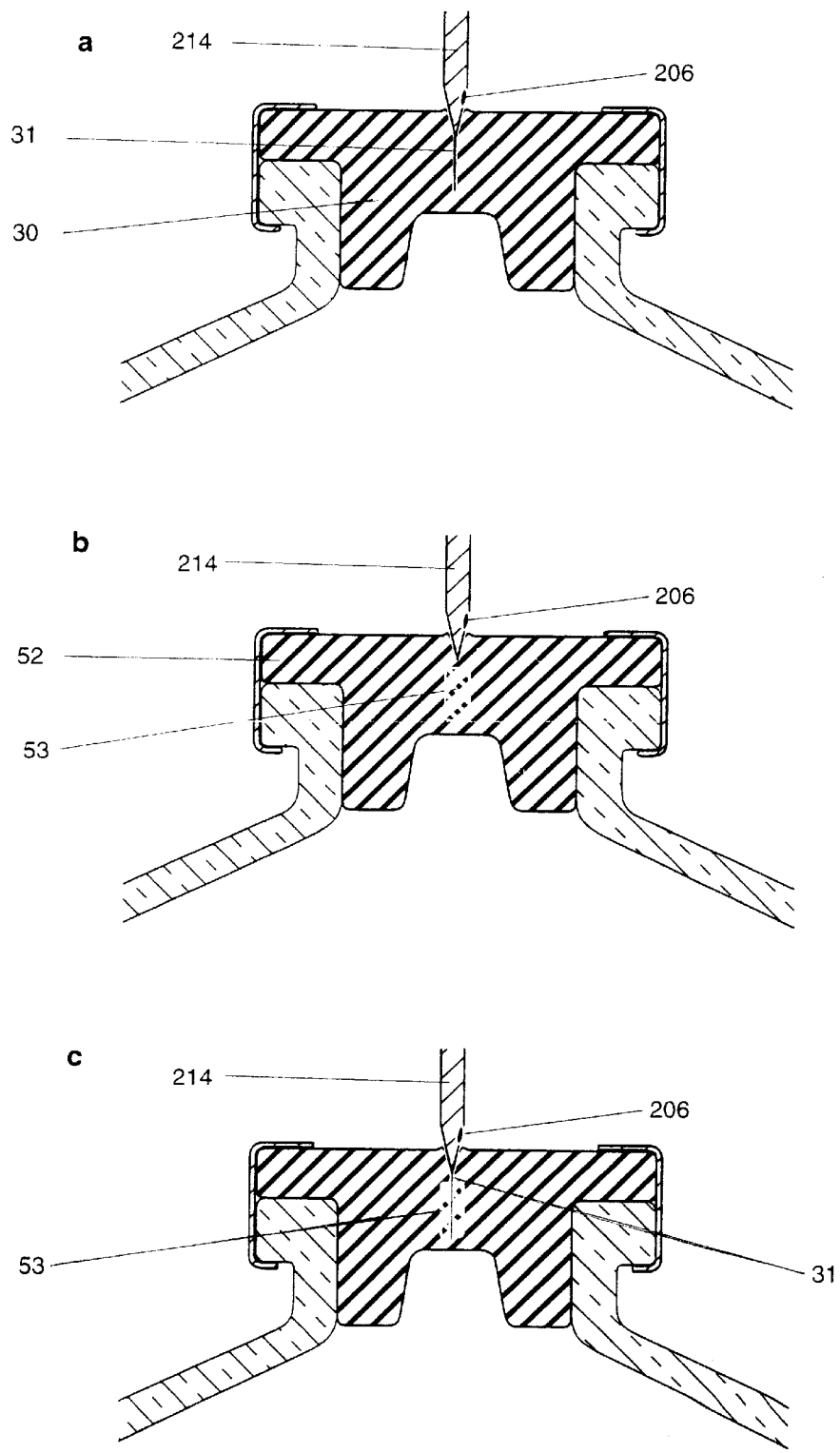
FIGS. 23a and 23b show combinations of a preferred embodiment of an inventive needle with a matched diaphragm which has undergone prechannelling and/or preweakening prior to needle insertion: a) diaphragm with a slit; b) diaphragm with a preweakened region.

FIGS. 23a–23b show examples of an inventive needle piercing an inventive (matched) diaphragm. FIG. 23a shows the process of inserting an inventive needle 214 with a recessed orifice 206 into an inventive diaphragm 30 with a channel 31 after relief of reversible compression. FIG. 23b shows a comparable process in an inventive diaphragm 52 with a partially weakened region 53.

Recessed-orifice needles are well-suited for being covered by a retractable sheath or cap as described in Disclosure #I and in U.S. Pat. No. 5,478,328, which are both incorporated by reference.

Testing of Needles, Diaphragms and their Combinations

The present invention also discloses arrangements for testing diaphragm, needle, and diaphragm/needle characteristics with and without varying degrees of reversible compression (at 2%, 4%, 6% . . . reversible reductions in diaphragm diameter). Data to be collected include the following.

A. Diaphragm Effectiveness

1) Bacterial counts of fluids stored under seemingly sterile conditions in containers covered by the diaphragms under study before, during and after needle or cannula insertion, with and without the application of varying degrees of reversible compression. This can be determined for the anticipated duration of clinical use. For example, an intravenous line with injection ports typically is replaced every 48 hours; a single-use drug bottle should be discarded within minutes to hours, while a multi-use vial contains a preservative and should be discarded within 30 days after first use.

Figure 24:
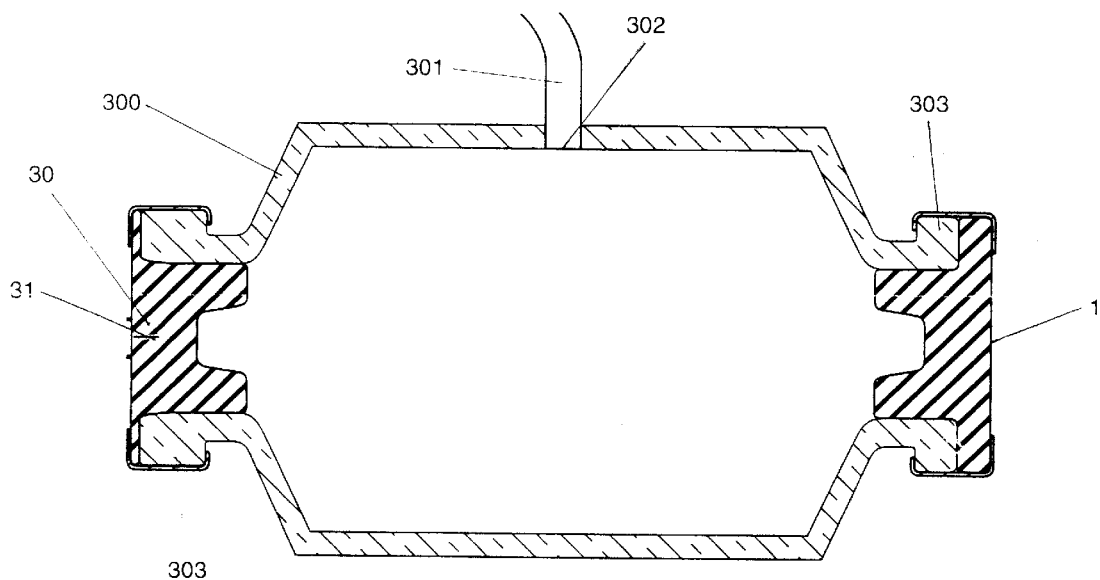
FIG. 24 shows an example of a device to simultaneously test and compare two or more diaphragms with respect to their leak-free integrity in the face of different pressures. The internal pressures may be increased by infusing fluid through a separate port.

2) Integrity of the diaphragm in comparative studies. FIG. 24 shows a setup for comparing the ability of two or more diaphragms to resist leaking under identical conditions while fluid is delivered via tubing 301 or a syringe through a sealed orifice 302 over the range of temperatures, rates, pressures, and infusate consistencies that may be encountered during actual use. In the example, there are two diaphragm testing sites 303; an inventive diaphragm 30 with channel 31 is being compared to standard diaphragm 1. Additionally, the diaphragm can be compared during and after needle insertion(s), with or without the application of enhanced compression. The inventive series of diaphragms will have integrity scores that exceed those of the needleless systems of the prior art since we are not limited to diaphragms which are penetrable by blunt cannulae from the time of manufacture (as described in the prior art). Likewise, the inventive systems will provide more secure engagement than blunt cannula needleless systems without supplemental means of securement. Whereas the prior art has not taught the use of needleless systems for covering openings wider than those covered by the diaphragms atop intravenous injection ports, an advantage of the present invention is to enable use of a wider range of diaphragm sizes as may be required to cover openings atop wide-mouthed bottles. Their integrity can be tested by modifying the size of the openings 303.

B. Needle Safety

1) Forces required for penetration of skin vs. diaphragm. A major objective of the design and testing processes of the present investigation is to increase healthcare worker safety by designing needle/diaphragm combinations which, upon testing and subsequent clinical use, demonstrate a high diaphragm/skin penetrability ratio. The goal is to design systems where the force required to pierce the diaphragm (typically in the range of 2 to 5 lbs but desirably less in certain embodiments) should be decidedly less than that required to pierce the skin.

2) We are introducing systems to test the relative penetrabilities. One such system is shown in FIGS. 25a and 25b.

Figure 25:
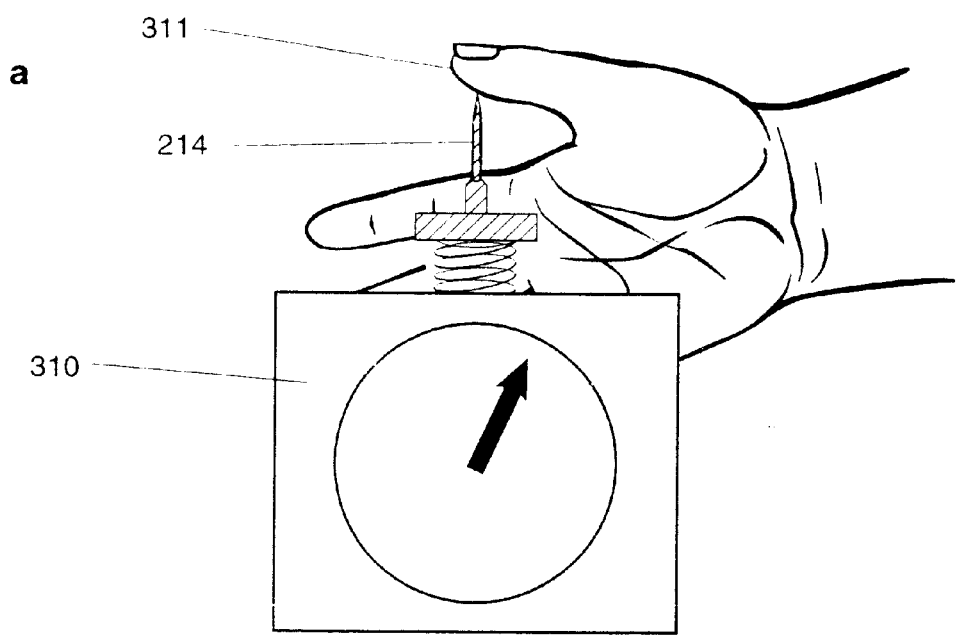
FIGS. 25a and 25b illustrate a device for determining the force required for a given needle to penetrate the skin (FIG. 25a) or a diaphragm (FIG. 25b) wherein the needle is mounted on a scale which records the force required for penetration.
Figure 25:
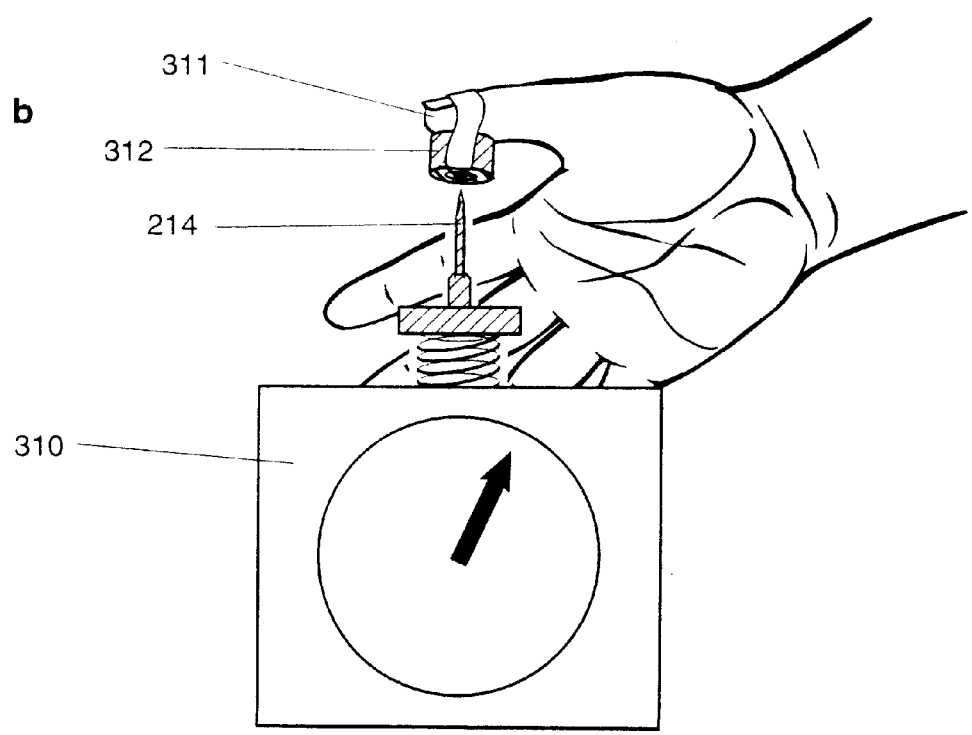

A needle 214 is attached to a scale 310 such that the tip of the needle is pointed outward so as to measure the force required to pierce (or penetrate to a specific depth) skin as of the thumb 311 (FIG. 25a) or a diaphragm 312; said diaphragm may be supported independently or attached to the thumb (as shown in FIG. 25b).

A more elaborate testing setup is illustrated in FIGS. 26a and 26b. A user's hand 313 is placed palm-side up under a strap (not shown) which limits the movement of all fingers except the thumb 311. The thumb is then secured by a restraining device, such as a ring 314, which is attached to a pressure transducer 315 which measures the force of subsequent thumb movement. (The use of an adductor pollicis force transducer in this manner is analgous to the means used to assess neuromuscular weakness in patients undergoing general anesthesia.) The needle 214 being tested is secured perpendicular to the thumb 311, with the needle point 210 touching or almost touching the palmar surface of the thumb 311 (FIG. 26a) or a diaphragm 312 attached to the thumb 311 (in FIG. 26b). (Alternatively, the needle 214 can be attached to the thumb 311 so as to puncture items placed in front of the thumb 311—not shown.) The thumb may be advanced voluntarily. However, it is more reliable to induce a standardized forward thumb movement with a nerve stimulator whose stimulating electrodes 317 are placed over the ulnar nerve. The stimulating current causes thumb adduction by inducing contraction of the adductor pollicis muscle. The degree of contraction depends on the number of contracting fibers, which in turn is dependent on the stimulating current. The stimulating current can be increased in 1–2 milliampere increments, while the resultant force of contraction is recorded. In the pictured embodiments, the needle 214 is maintained in a fixed position in front of the thumb 311.

The standard stimulus used to elicit nerve firing in the assessment of neuromuscular function in the clinical setting (0.2 milliseconds in duration repeated at a rate of 0.1 Hz=once every 10 seconds) was used for our initial trial. It reliably induces movement consistent with that which is associated with accidental self-puncture. Stimuli of different duration and/or repetitive stimuli may be utilized. Preload may be added, as indicated, to alter the amount of thumb movement. Even greater reliability may be achieved in anesthetized subjects (who will not resist thumb advancement).

Figure 26:
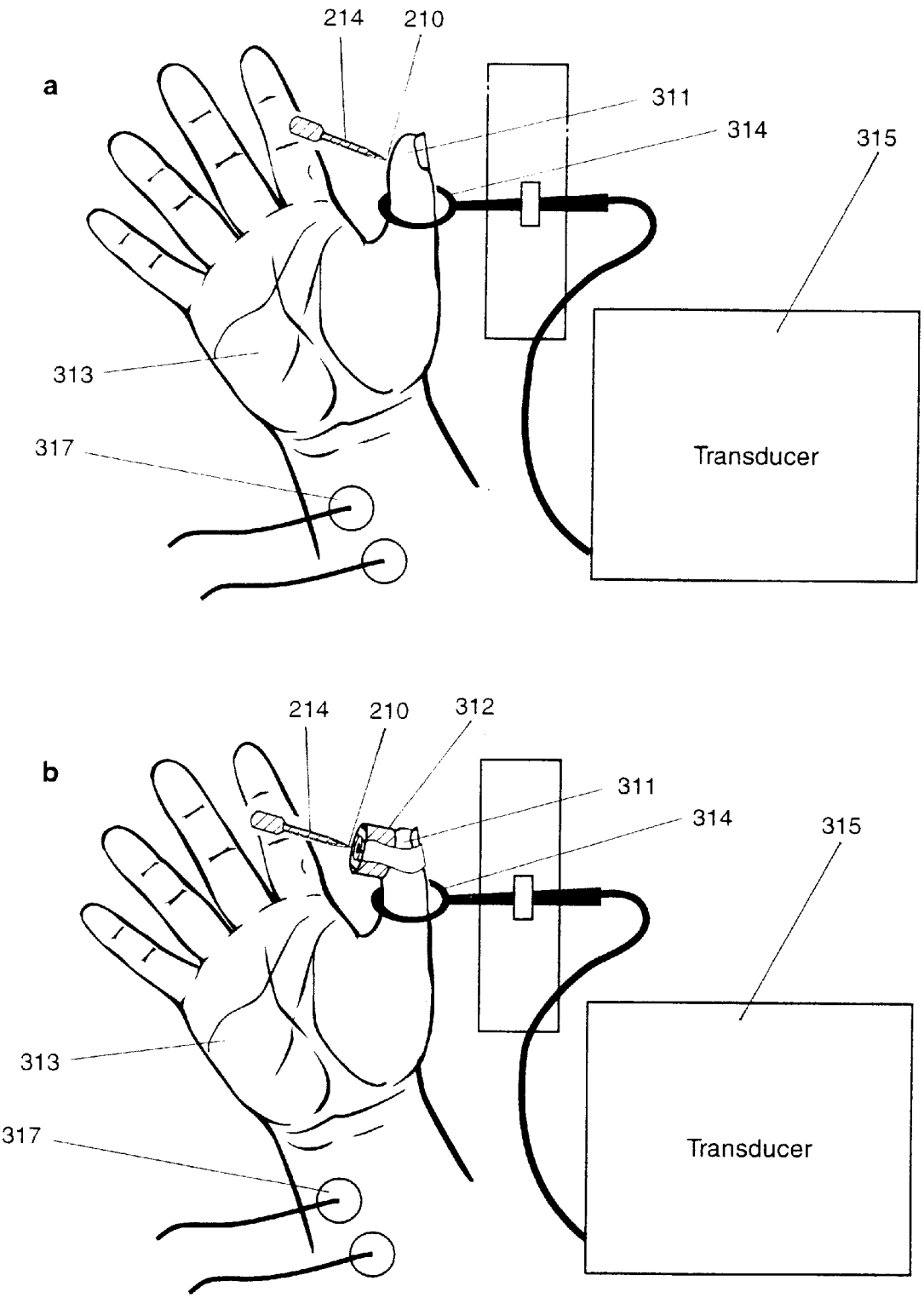
FIGS. 26a and 26b illustrate a more elaborate arrangement for testing the penetrability of skin and diaphragms. The illustrated mechanism is designed to provide involuntary movements of the thumb by contraction of the adductor pollicis muscle as a result of stimulation of the ulnar nerve.

During testing with the setup illustrated in FIG. 26, we found that a standard open-bevel needle consistently punctured the skin such that blood appeared (and pain was felt) at 9–10 mm Hg pressure. (Lesser forces, due to lower currents, did not cause skin puncture.) In contrast, a sharp closed tip needle required a pressure of >15 mmHg to puncture the skin (and this was to a depth which did not advance the orifice into the skin).

Needles and diaphragms designed in accordance with the present invention or for other purposes can be tested and rated according to the aforementioned system, for example. Such ratings may include, but are not necessarily limited to, absolute force requirements for causing puncture of skin or diaphragm, as well as relative force requirements for piercing skin vs. diaphragm. The forces required for penetration to a depth that allows a needle's orifices to be advanced through the skin (and thus deliver an infectious inoculum) may be determined in a variety of ways, including recording the aforementioned penetrability studies on film. We also are in a unique position to test diaphragms in compressed and uncompressed states and to determine the forces required in each state for penetration by standard needles, inventive needles, and blunt cannulae.

Statistical data will include mean, median, standard deviation, standard error, as well as the confidence intervals, and coefficients of repeatability and variation. Embodiments of the inventive series will be compared to the Strong Diaphragm/Dangerous Needle and Weak Diaphragm/Safe Cannula combinations of the prior art. Ideally, the force required to puncture the skin should be many times greater than (at least double) that required to penetrate a matched diaphragm. Needles also may be rated according to their incidence of skin puncture in clinical settings. Parametric data will be analyzed by paired t-testing and analysis of variance with appropriate modifications for multiple comparisons. Non-parametric data may be assessed using ranking techniques. Incidence (e.g. of skin penetration among different needles in different contexts) may be compared using Chi-squared analysis.

The relative simplicity of the aforementioned testing systems enables rapid testing of a wide range of needles, cannulae, and diaphragms. If deemed indicated, one can utilize the teaching of the prior art to guide initial testing. For example, for a needle with a diameter of 0.10 inch (0.254 cm), we will begin testing with a slit of the diameter recommended for absolutely blunt cannula in the prior art. The greater sharpness of the inventive needles will allow progressive decrease of the size of the slit to attain increased diaphragm integrity while seeking to ensure healthcare worker safety.

Thus, this disclosure (as well as the accompanying disclosures of this three-part series) teaches a combined testing procedure which addresses both testing of diaphragm integrity and penetrability as well as relative needle safety using combined indices, in the design and testing of needle/diaphragm configurations.

What is claimed is:

1. A process of reversibly increasing a compression pressure on a compromised diaphragm, which comprises the steps of:

compromising the diaphragm to enhance its penetrability;

then applying peripheral pressure the diaphragm, to seal the diaphragm;

then reducing the pressure; and then permitting an insertion member to penetrate the diaphragm in its compromised region for fluidic communication after said reduction of the pressure.

2. The process of claim 1 wherein the diaphragm is compromised by prechannelling.

3. The process of claim 1 wherein the diaphragm is compromised by preweakening.

4. The process of claim 1, wherein the sealability, integrity and hence shelf-life of the compromised diaphragm are augmented by reversible application of enhanced compression pressure.

5. The process of claim 4, wherein the diaphragm is compromised by prechanneling.

6. The process of claim 4, wherein the diaphragm is compromised by preweakening.

7. The process of claim 1 wherein a diaphragm region about 0.20–0.23 inches in diameter is reversibly reduced by said compression to about 0.17 to 0.20 inches in diameter.

8. The process of claim 1, wherein a diameter of the diaphragm is reduced by the compression pressure to about 60–80% of its original diameter.

9. The process of claim 1, wherein non-symmetrical pressure is applied around the diaphragm so as to selectively bias a prechannelled region of the diaphragm into a closed position.

10. The process of claim 9, wherein the pressure is applied by diametrically opposed tabs and grooves arranged around the diaphragm, wherein upon engagement, sides of a slit in the compromised region of the diaphragm become biased in the closed position.

11. The process of claim 9, wherein the pressure is applied by one or more removable pegs, wherein the pegs occupy a space between an inner wall of the receptacle and an outer surface of the diaphragm, and insertion of the pegs causes approximation of sides of a preslit region in the diaphragm.

12. The process of claim 1, wherein the pressure applied to the compromised region is symmetrical.

13. The process of claim 12, wherein the insertion member is a needle with an open tip which has an angle greater than approximately a 45° angle to a longitudinal axis of the needle.

14. The process of claim 12, wherein the insertion member is a needle with an open tip which has a rounded or blunted distal tip.

15. The process of claim 12, wherein the insertion member is a needle which has a closed tip and one or more recessed orifices.

16. The process of claim 12, wherein the insertion member is a blunt cannula, wherein the blunt cannula requires more extensive preslitting and/or a greater degree of preweakening than does a needle for effective diaphragm penetration.

17. The process of claim 12, wherein the diaphragm is prechannelled and the insertion member is a needle, wherein the needle penetrates the diaphragm in the absence of reversibly augmented compressive pressure.

18. The process of claim 12, wherein the diaphragm is preweakened and the insertion member is a needle, wherein the needle penetrates the diaphragm in the absence of reversibly augmented compressive pressure.

19. The process of claim 12, wherein the diaphragm is preslit and the insertion member is a blunt cannula, wherein the cannula penetrates the diaphragm in the absence of reversibly auginelited compressive pressure.

20. The process of claim 12, wherein the diaphragm is preweakened and the insertion member is a blunt cannula, wherein the cannula penetrates the diaphragm in the absence of reversibly augmented compressive pressure.

21. The process of claim 12, further comprising means for identifying whether the pressure has been reduced.

* * * * *